United States Patent [19]
Rohrberg

[11] Patent Number: 5,572,995
[45] Date of Patent: Nov. 12, 1996

[54] FLOATATION ENHANCED SELF-EXAMINATION SYSTEM

[76] Inventor: Roderick G. Rohrberg, 2742 W. 234th St., Torrance, Calif. 90505

[21] Appl. No.: 456,438

[22] Filed: Jun. 1, 1995

Related U.S. Application Data

[63] Continuation-in-part of Ser. No. 123,490, Sep. 17, 1993, Pat. No. 5,474,064.
[51] Int. Cl.$^6$ ...................................................... A61B 5/00
[52] U.S. Cl. ............................................................. 128/630
[58] Field of Search .............................. 128/630, 660.01, 128/660.07, 663.01, 915; 434/267, 275

[56] References Cited

U.S. PATENT DOCUMENTS

| | | | |
|---|---|---|---|
| 4,282,880 | 8/1981 | Gardineer et al. | 128/915 X |
| 4,347,850 | 9/1982 | Kelly-Fry et al. | 128/915 X |
| 4,545,385 | 10/1985 | Pirschel | 128/915 X |
| 4,737,109 | 4/1988 | Abramson | 434/267 |
| 4,793,354 | 12/1988 | Wright et al. | 128/630 |
| 4,867,686 | 9/1989 | Goldstein | 434/267 |
| 5,207,582 | 5/1993 | Michelson | 434/416 |
| 5,479,661 | 1/1996 | Fingleson et al. | 2/69 |

*Primary Examiner*—Francis Jaworski
*Attorney, Agent, or Firm*—Anglin & Giaccherini

[57] ABSTRACT

The Floatation Enhanced Self-Examination System comprises apparatus and methods for performing a finger tip examination of portions of the human body that exploits the beneficial effects of floatation. Although the method is especially useful for conducting a self-examination of the female breast, tissues of the male abdomen and testicles may also be examined using the present invention. In the preferred embodiment of the invention, a patient relaxes while substantially immersed in hot water. When the breast is submerged, the buoyancy of the breast tissue in the water counteracts the effects of gravity. The buoyancy of the water enhances the ability of the patient herself or a second person to test the breast tissue to detect abnormalities. In accordance with a preferred embodiment of the present invention called the Finger Walk$^{SM}$, the examination is performed utilizing a random, repetitive, palpitating pressure using the tips of the examiner's finger.

12 Claims, 23 Drawing Sheets

BUST MOLD MEASUREMENTS
DIGITIZED NUMBERS OF MOLD
RADIAL POSITION - 30° INCREMENTS

**BUST MOLD #1
LEFT BREAST**

| ELEVATION | 0° | 30° | 60° | 90° | 120° | 150° | 180° | 210° | 240° | 270° | 30° | 330° | 360° |
|---|---|---|---|---|---|---|---|---|---|---|---|---|---|
| .000 | (NIPPLE) | | | | | | | | | | | | |
| .100 | .272 | .240 | .225 | .215 | .204 | .174 | .175 | .185 | .190 | .201 | .233 | .266 | .272 |
| .200 | .583 | .545 | .446 | .346 | .277 | .229 | .213 | .246 | .290 | .368 | .467 | .549 | .578 |
| .300 | .841 | .800 | .687 | .576 | .484 | .418 | .403 | .426 | .483 | .590 | .694 | .785 | .841 |
| .400 | 1.039 | .986 | .863 | .739 | .670 | .605 | .573 | .573 | .651 | .742 | .857 | .971 | 1.038 |
| .500 | 1.206 | 1.145 | 1.029 | .918 | .838 | .780 | .741 | .729 | .777 | .872 | 1.001 | 1.133 | 1.205 |
| .600 | 1.346 | 1.286 | 1.182 | 1.087 | 1.032 | .957 | .905 | .879 | .915 | 1.010 | 1.164 | 1.297 | 1.353 |
| .700 | 1.486 | 1.410 | 1.314 | 1.249 | 1.205 | 1.146 | 1.070 | 1.019 | 1.053 | 1.148 | 1.314 | 1.436 | 1.490 |
| .800 | 1.609 | 1.521 | 1.440 | 1.389 | 1.358 | 1.312 | 1.220 | 1.161 | 1.172 | 1.281 | 1.443 | 1.573 | 1.608 |
| .900 | 1.722 | 1.623 | 1.549 | 1.523 | 1.513 | 1.466 | 1.376 | 1.292 | 1.284 | 1.396 | 1.563 | 1.686 | 1.722 |
| 1.000 | 1.818 | 1.715 | 1.650 | 1.638 | 1.640 | 1.610 | 1.515 | 1.447 | 1.398 | 1.506 | 1.673 | 1.788 | 1.820 |
| 1.100 | 1.904 | 1.793 | 1.744 | 1.743 | 1.768 | 1.744 | 1.649 | 1.529 | 1.503 | 1.609 | 1.756 | 1.868 | 1.905 |
| 1.200 | 1.981 | 1.866 | 1.831 | 1.840 | 1.882 | 1.871 | 1.777 | 1.647 | 1.608 | 1.699 | 1.852 | 1.953 | 1.980 |
| 1.300 | 2.040 | 1.939 | 1.912 | 1.928 | 1.973 | 1.983 | 1.890 | 1.754 | 1.690 | 1.782 | 1.928 | 2.012 | 2.042 |
| 1.400 | 2.096 | 2.004 | 1.984 | 1.997 | 2.062 | 2.092 | 2.010 | 1.854 | 1.783 | 1.857 | 1.994 | 2.083 | 2.097 |
| 1.500 | 2.144 | 2.058 | 2.056 | 2.084 | 2.140 | 2.202 | 2.135 | 1.962 | 1.867 | 1.924 | 2.061 | 2.140 | 2.143 |
| 1.650 | 2.209 | 2.143 | 2.150 | 2.180 | 2.259 | 2.358 | 2.327 | 2.123 | 1.979 | 2.014 | 2.149 | 2.209 | 2.205 |
| 1.800 | 2.260 | 2.213 | 2.242 | 2.265 | 2.359 | 2.511 | 2.548 | 2.289 | 2.077 | 2.093 | 2.219 | 2.270 | 2.257 |
| 1.950 | 2.299 | 2.285 | 2.318 | 2.348 | 2.456 | 2.678 | 2.795 | 2.482 | 2.189 | 2.159 | 2.281 | 2.317 | 2.299 |
| 2.100 | 2.333 | 2.340 | 2.385 | 2.423 | 2.550 | 2.864 | 3.113 | 2.690 | 2.291 | 2.231 | 2.347 | 2.370 | 2.333 |
| 2.250 | 2.365 | 2.377 | 2.442 | 2.487 | 2.633 | 3.074 | 3.474 | 2.946 | 2.403 | 2.287 | 2.400 | 2.420 | 2.368 |
| 2.400 | 2.427 | 2.475 | 2.476 | 2.544 | 2.722 | 3.316 | 3.810 | 3.229 | 2.517 | 2.368 | 2.458 | 2.487 | 2.427 |
| 2.500 | 2.482 | 2.471 | 2.496 | 2.572 | 2.787 | 3.509 | 3.975 | 3.412 | 2.615 | 2.418 | 2.508 | 2.586 | 2.486 |
| 2.550 | 2.527 | 2.498 | 2.507 | 2.584 | 2.830 | 3.613 | 4.040 | 3.492 | 2.669 | 2.447 | 2.534 | 2.583 | 2.527 |
| 2.600 | 2.577 | 2.528 | 2.522 | 2.600 | 2.872 | 3.710 | 3.937 | 3.577 | 2.720 | 2.478 | 2.565 | 2.615 | 2.573 |
| 2.650 | — | 2.567 | 2.530 | 2.611 | 2.908 | 3.791 | 4.168 | 3.668 | 2.801 | 2.517 | 2.599 | 2.659 | — |
| 2.700 | — | 2.593 | 2.543 | 2.628 | 2.964 | 3.868 | 4.203 | 3.762 | 2.882 | 2.559 | 2.633 | 2.715 | — |
| 2.750 | — | 2.620 | 2.557 | 2.642 | 3.013 | 3.902 | 4.239 | 3.852 | 2.992 | 2.606 | 2.679 | 2.762 | — |
| 2.800 | — | — | — | — | — | — | — | 3.941 | 3.136 | 2.668 | 2.729 | 2.810 | — |

*FIG. 39*

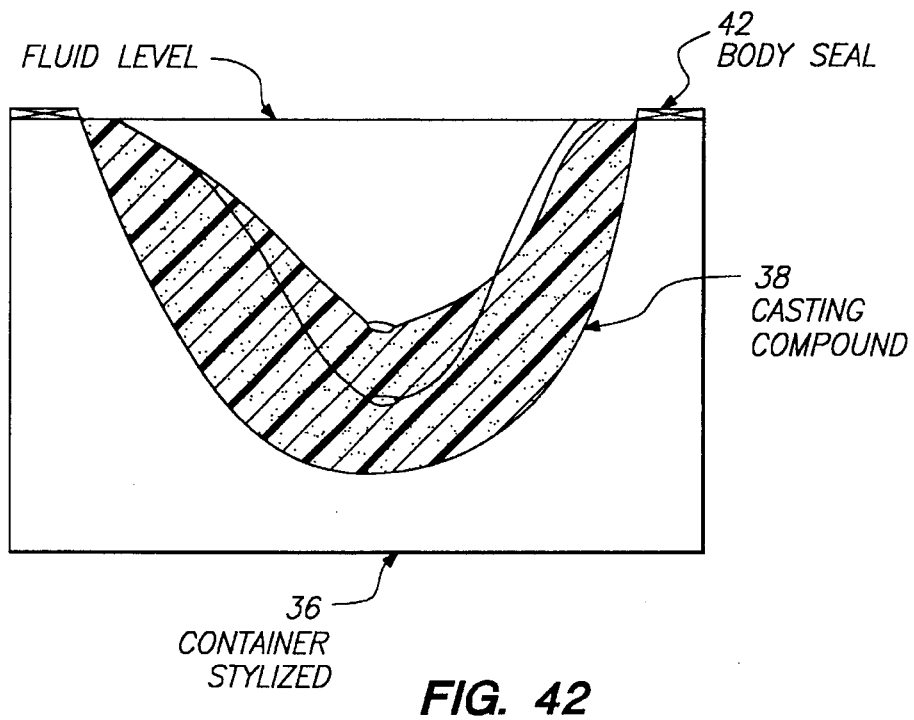
FIG. 42
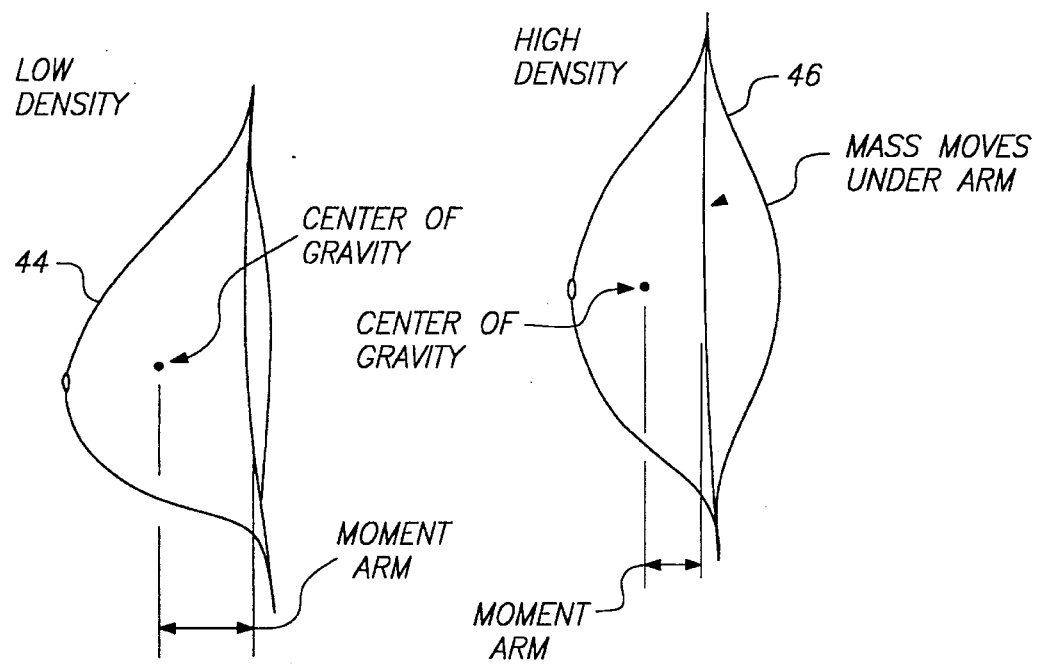
FIG. 43  FIG. 44

FLOATATION ENHANCED SELF-EXAMINATION SYSTEM

CROSS-REFERENCE TO A RELATED PATENT APPLICATION & CLAIM FOR PRIORITY

The present patent application is a Continuation-in-Part application, and is related to a commonly-owned pending patent application entitled Breast Self-Examination Floatation System by Roderick G. Rohrberg, which was filed on 17 Sep. 1993 and is now U.S. Pat. No. 5,474,064. The inventor hereby claims the benefit of priority under Section 120 of Title 35 of the United States Code of Laws for any and all subject matter which is commonly disclosed in the Present Application and in the pending patent application assigned U.S. Ser. No. 08/123,490.

FIELD OF THE INVENTION

The present invention pertains to self-examination of various parts of the human body. More particularly, the present invention utilizes novel finger tip examination methods in a floatation environment which levitates portions of the body to enhance awareness of body's condition. The combination of the floatation effect and the relaxing environment created by a hot bath permit the internal structure of the examined tissue to shift position readily and painlessly permitting greater access to any abnormality that could potentially be obscured by normal internal breast structure. Present procedures are unable to offer the enhanced detection capabilities offered by the novel Finger Walk$^{SM}$ methods described below.

BACKGROUND OF THE INVENTION

According to a recent study by the American Cancer Society, 46,000 women in the United States will die in 1993 from breast cancer. (From the 1993 *World Almanac*, published by Pharos Books.) Recent advances in diagnostic techniques and surgical treatments have helped to reduce the mortality rate due to breast cancer, but this disease is still the third greatest cause of death among women in this country. A variety of mammographic systems which employ X-rays and ultrasound have been developed over the past few decades, but this equipment is generally very large, prohibitively expensive and requires a trained technician to operate them. As an example, the minimum price of an ultrasonic imaging system sold by Acuson of Mountain View, Calif. exceeds $200,000. Several documents noted below disclose various systems that pertain to equipment that may be used for different kinds of medical diagnosis.

In his U.S. Pat. No. 4,130,112, Frazer describes an apparatus for ultrasonic scanning of a breast or other tissue. This invention includes a cavity for receiving the patient's breast, and a vacuum for drawing the breast into intimate contact with the walls of the cavity. The walls enclose ultrasonic transducers that are employed to create an image of the breast tissue.

U.S. Pat. No. 4,135,497 issued to Meyers et al. reveals an apparatus for detecting temperature variations over selected regions of living tissue. The inventors state that the method disclosed in their patent is useful for detecting malignant tissue in the breasts.

U.S. Pat. No. 4,206,763 issued to Pedersen discloses a device and a method for ultrasonic examination for carcinoma of the breast. Pedersen employs a compartment in which water is drawn upward by suction over the breast. An ultrasonic transducer then revolves around the breast to obtain complete 360 degree scans. A pleated flexible bag 12 pulls the breast into a water bath compartment 4 when the water bath compartment 4 is evacuated by a pair of bellows 16. (See Column 1, Lines 60–68; Column 3, Lines 23–51 and Column 4, Lines 4 & 5.)

U.S. Pat. No. 4,252,125 issued to Iinuma describes an ultrasonic diagnosing apparatus that utilizes a receptacle 11 filled with warm water 12. An ultrasonic probe 14 makes an image of the breasts, which are pressed against a flexible membrane 18 that is stretched in front of the probe. (See Column 1, Lines 65–68 and Column 2, Lines 1–7.)

U.S. Pat. No. 4,341,222 issued to Gardineer et al. relates to a patient support system for orienting a woman's breast over an ultrasound scanner. The patient is shown bent over a pool of water 20 that is positioned over a scanning transducer 14. (See Column 5, Lines 62–68 and Column 6, Lines 1–4.) The water serves as a transmission medium for the ultrasonic waves. (See Column 2, Lines 15 & 16.)

U.S. Pat. No. 4,347,850 issued to Kelly-Fry et al. discloses a direct water coupling device for ultrasound scanning. A tank 10 is placed in a sealed position about the perimeter of the breast area while the patient is in a supine position. (See FIG. 3 & Column 4, Lines 37–38.)

U.S. Pat. No. 4,545,385 issued to Pirschel describes an apparatus for ultrasonic examination of body parts using a fluid container and an ultrasound scanning system. (See FIG. 1.) A liquid-filled basin 6 serves as an acoustic coupling. (See Column 3, Lines 4–5 & Column 3, Lines 24–25.)

U.S. Pat. No. 4,657,021 issued to Perry et al. concerns an apparatus which he claims enhances the sense of touch when placed between the fingertips of the user and the object being touched. A liquid lubricant 13 is captured inside a sealed enclosure 10 made from a pliable, elastic material. (See Column 2, Lines 36–40 and Column 3, Lines 4–18.)

U.S. Pat. No. 4,873,982 issued to Morrison contains an discussion of an examination garment that may be used to feel for lumps under the skin. (See FIGS. 1 and 3.)

U.S. Pat. No. 4,917,096 issued to Englehart et al. reveals the details of a portable ultrasonic probe. A fluid-filled enclosure is coupled to a handled portion which houses a drive motor. (See FIG. 3.) The probe 20 includes a fluid-filled enclosure 34. (See Column 4, Lines 30–31.)

U.K. patent application No. 2,111,347A by Robert Cribbs pertains to a method of pulse examination using a container that holds a liquid couplant. The container is placed about the breasts of a female torso, and breast tissue is scanned using ultrasound.

A brochure published by Metrix Incorporated of Deerfield, Ill. presents specifications for echo-scan and echo-trace ultrasonic analyzers. The brochure describes how high frequency, short duration electromechanical pulses emitted by special transducers in direct or indirect contact with a portion of the human body can produce visual information.

In her book entitled *Dr. Susan Love's Breast Book*, Susan M. Love describes conventional palpating techniques for breast self-examinations. (See pp. 21–31).

The problem of providing a low-cost yet effective device for self-examination of portions of the human body has presented a major challenge to medical technicians and imaging experts. The development of methods and apparatus that enhance the prospects of detecting abnormalities during self-examinations would constitute a major technological advance and would satisfy a long felt need within the health-care field.

SUMMARY OF THE INVENTION

The *Floatation Enhanced Self-Examination System* comprises apparatus and methods for performing a finger tip examination of portions of the human body utilizing the beneficial effects of floatation. The method is especially useful for conducting a self-examination of the female breast. In the preferred embodiment of the invention, a patient relaxes in a tub filled with hot water. The physical relaxation created by the bath brings about a concomitant state of mental relaxation. When the breast is substantially submerged, the buoyancy of the breast tissue in the water counteracts the effects of gravity. The buoyancy of the water enhances the ability of the patient herself or a second person to probe the breast tissue to detect abnormalities.

By using the Finger Walk$^{SM}$ method of the preferred embodiment, aberrations in the breast may be discovered at an early stage. In the preferred embodiment of the invention, gentle pressure is applied systematically to localized areas using the finger tips. This pressure scans the breast tissue in a repetitive, palpitating motion.

The floatation effect and the relaxing environment created by a hot water bath endows the examiner with an exceptional ability to detect abnormalities in the patient. The methods described and claimed below permit finger tip penetration of an unusual order of magnitude that are not possible to realize using conventional techniques. The floatation effects blossom the breast into a full and very manageable shape that permits the unique Finger Walk$^{SM}$ method to detect abnormalities that are not generally sensed by conventional techniques.

The combined effects of floatation and relaxation permit the penetration of the finger tips of an unusual order of magnitude that present methods ignore. The floatation forces blossom the breast into a full and very manageable shape that permits the unique Finger Walk$^{SM}$ method to detect abnormalities heretofore unknown to industry.

An appreciation of other aims and objectives of the present invention and a more complete and comprehensive understanding of this invention may be achieved by studying the following description of preferred embodiment and alternative embodiments and by referring to the accompanying drawings.

BRIEF DESCRIPTION OF THE DRAWINGS

In FIG. 6, the patient is shown in a lateral view in an upright position and the examiner is checking tissue near the rib cage.

FIG. 38 is a cross-sectional plot of a female breast, while FIG. 39 is a table that contains bust mold measurements for the breast shown in FIG. 38.

FIG. 42 is a side view of the container shown in FIG. 41.

FIGS. 43 and 44 depict profiles of low and high density castings a female breast.

DETAILED DESCRIPTION OF PREFERRED & ALTERNATIVE EMBODIMENTS

Figure 1:
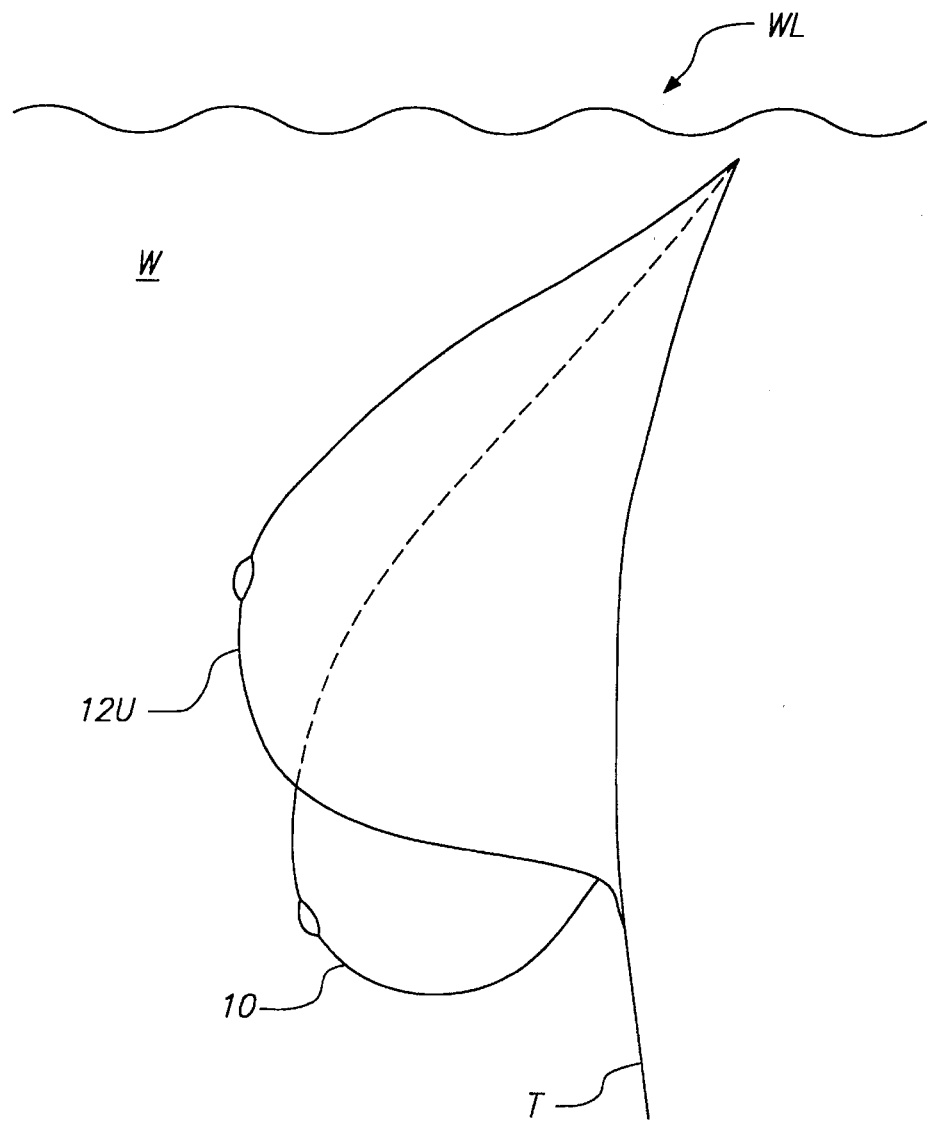
FIG. 1 is a cross-sectional view which compares a female breast in a pendent position and in the levitated position which occurs when it is immersed in water.

FIG. 1 furnishes cross-sectional, superimposed views of a single female breast. In this figure, the patient is positioned in an upright posture, leaning forward at an angle of approximately five to fifteen degrees. In one view, the breast is shown extending from the torso T in its normal, unsupported and pendent position 10. The second view shows the position of the same breast when the breast is immersed in water W. This immersion is accomplished by having the patient sit in a tub filled with hot water. This second position, indicated by the reference character 12U, is the natural or undetected position of the breast under the influence of the levitating effects of the water W. When the breast is substantially submerged below the water line WL, the buoyancy of the breast tissue in the water counteracts the effects of gravity. Although other fluids such as salt-water may be employed to exaggerate the differences in density between the breast and the fluid medium, and to further lift the breast tissue, ordinary hot water is utilized in the preferred embodiment of the invention. According to the preferred embodiment of the invention, the best temperature range for the hot water is 101 to 104 degrees Fahrenheit.

This buoyancy or "floatation" effect enhances the ability of the patient herself or a second person to test the breast tissue to detect abnormalities. By using the Finger Walk$^{SM}$ method of the preferred embodiment, aberrations in the breast may be discovered at an early stage.

Figure 2:
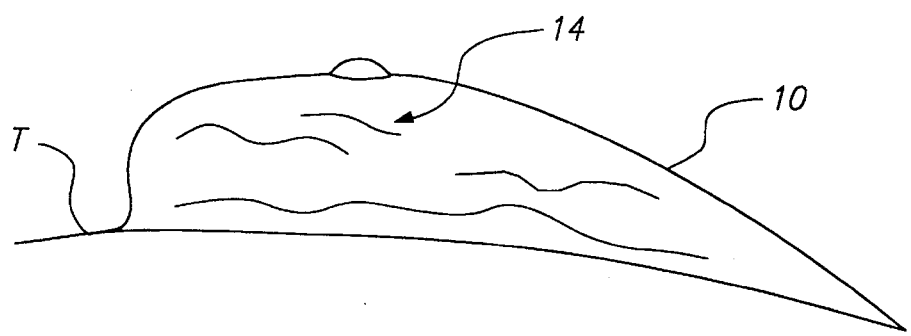
FIGS. 2 and 3 are cross-sectional illustrations of a female breast in a supine position in its undetected non-floatation position.
Figure 3:
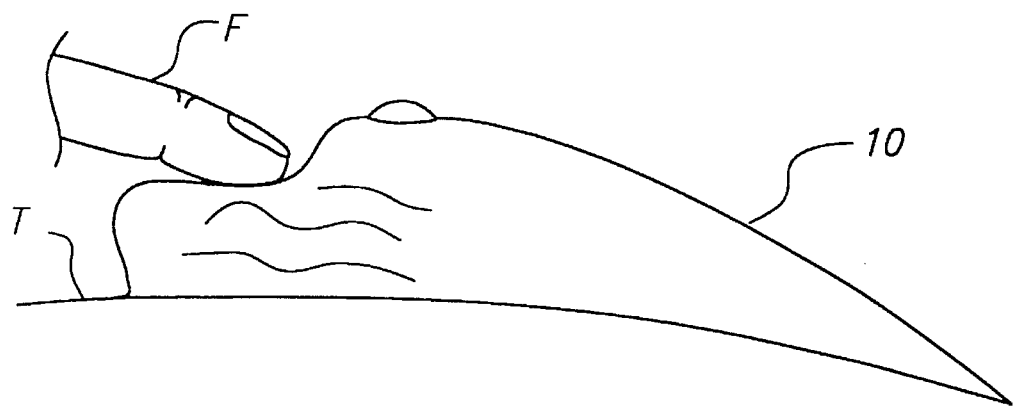

FIGS. 2 and 3 provide additional cross-sectional illustrations of a female breast which is not immersed in water. In FIG. 2, the patient is reclining on her back in a supine posture. As a consequence, the breast occupies a normal flattened position. The collapsed, overlapping internal structure of the breast is identified by reference character "14". FIG. 3 illustrates the finger F of an examiner who gently engages or palpitates the breast as shown in FIG. 2 to detect abnormalities. In this Specification, the term "examiner" refers to both the patient herself or to a second person who may stroke the tissue in an attempt to detect abnormalities. Although the preferred embodiment of the invention pertains to the examination of the female breast, the present invention may be beneficially employed to examine a variety of body parts of both genders, including tissues of the male abdomen and testicles.

Figure 4:
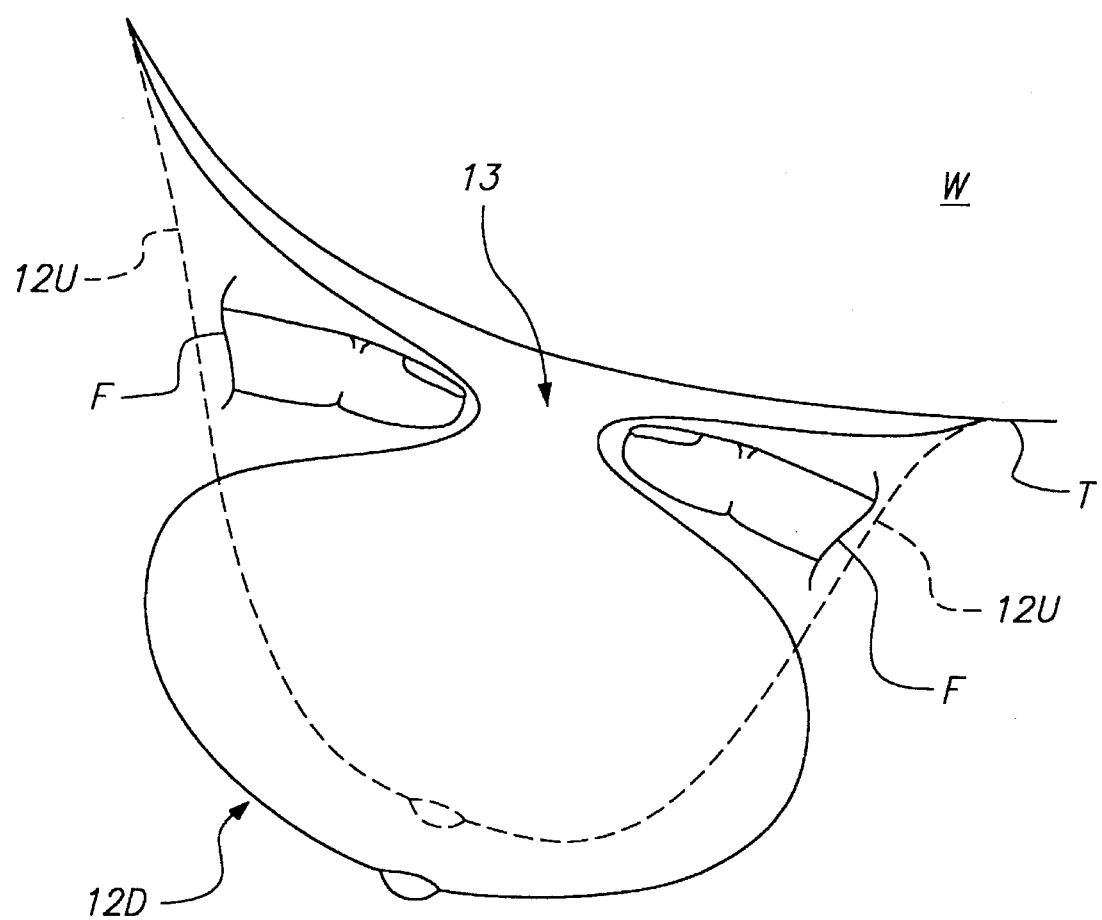
FIGS. 4 and 5 show cross-sectional depictions of a female breast in a top view in floatation in both an undetected pendent position and in a deflected position that occurs during examination.
Figure 5:
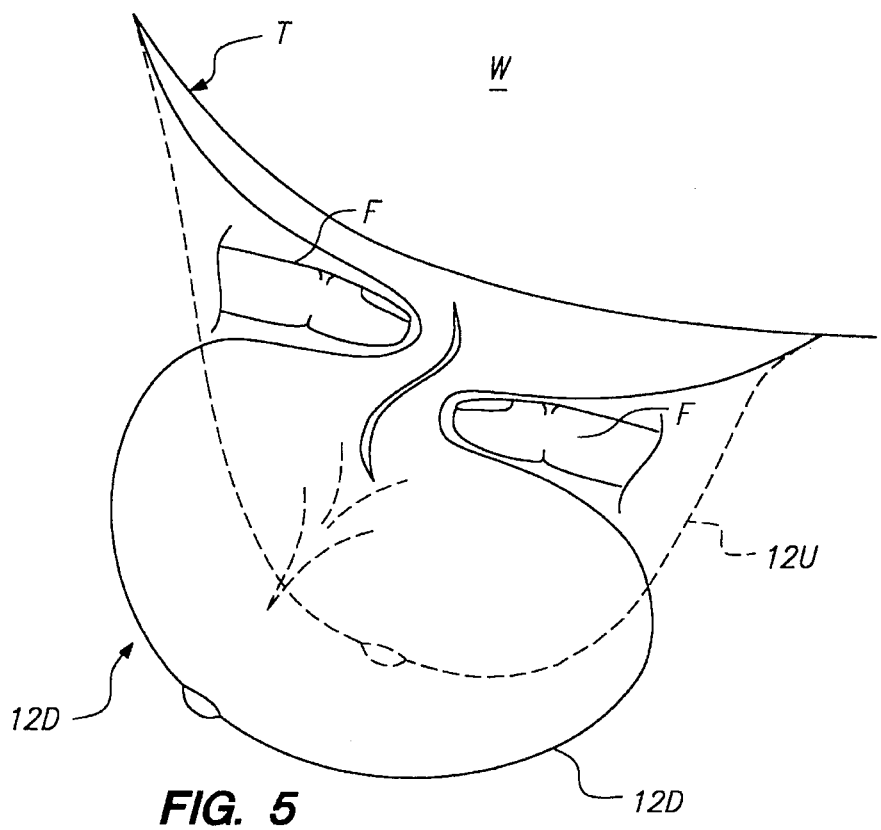

FIGS. 4 and 5 provide two superimposed views of a single breast. The perspective in both cross-sectional views is from the overhead position, looking down into the water bath towards the immersed breast. In both FIGS. 4 and 5, the patient is in an upright position, leaning forward approximately five to fifteen degrees. One depiction, indicated by 12U, represents the breast in a natural undetected position under the effects of floatation. The second depiction, indicated by 12D, illustrates the shape of the breast after it has been deflected by the gentle probing action of the examiner's finger tips FT. The constricted portion of the breast that lies between the examiner's finger tips FT is indicated by reference character 13. It is this ability to obtain the narrow constriction that greatly enhances the sensitivity of the detection procedure.

In the preferred embodiment of the invention, slight pressure is applied to the breast tissue simultaneously using the tips of the fingers of both hands. The hands are placed in a position that allows the tips of the fingers of opposite hands to face each other. This arrangement of the fingers is referred to as the "opposing" position of the fingertips. When the tips of the fingers are used to probe the tissue in this opposing position, the capacity to detect abnormalities is enhanced. The heightened sensitivity results from the improved sensory ability of the finger tips to discover an abnormality when it is caught between the two opposed surfaces of the finger tips.

Unlike conventional examination methods, the floatation environment allows the breast to assume its full, undistorted and natural position and shape. Conventional breast examination procedures often involve the use of the supine position and other positions which introduce muscle and tissue distortions caused by the placement of the patient's arms over her head. Other tissue distortions are caused by gravity. The present invention eliminates these unwanted effects by counteracting all forces which would tend to block the patient's ability to perform an effective examination.

Figure 6:
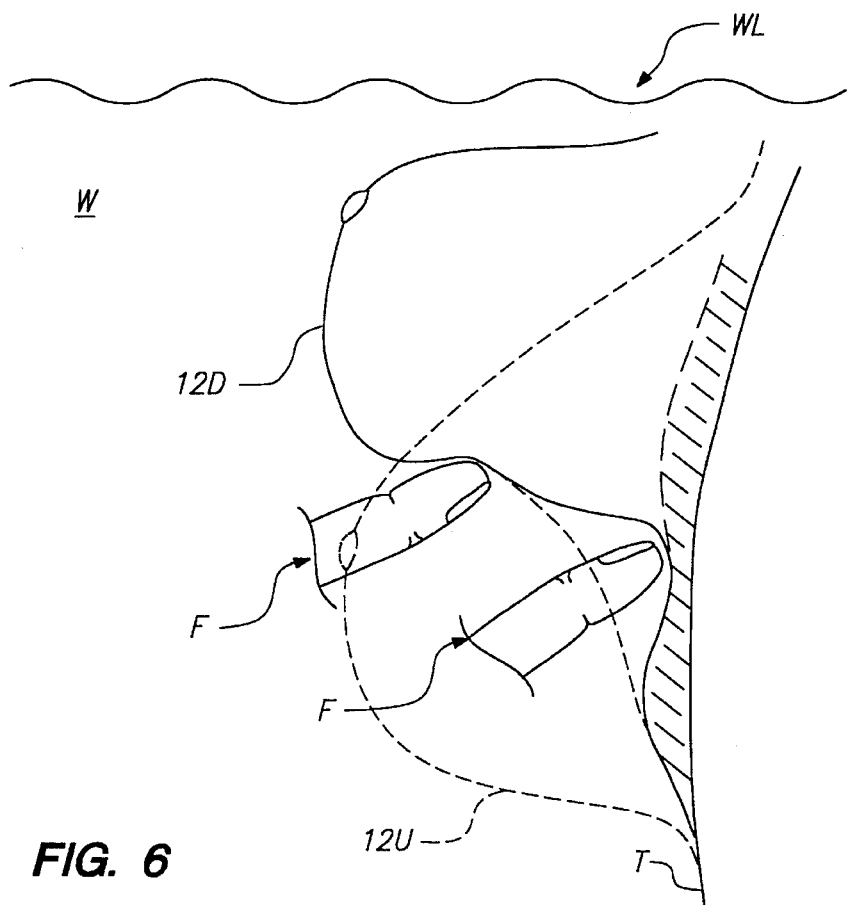
FIG. 6 provides a cross-sectional representation of a female breast in floatation in both undetected and deflected positions.

FIG. 6 presents side views of a female breast under floatation forces. In this view, the patient is in an upright position, leaning forward slightly (approximately five to fifteen degrees). The outline marked "12U" represents the position of the levitated breast without any deflection forces introduced by the examiner. The outline marked "12D" represented the position of the levitated breast after it has been deflected by the examiner. The outline indicated by reference character 12D reveals how the breast can be gently floated out of the way exposing the structure near the rib cage.

Figure 7:
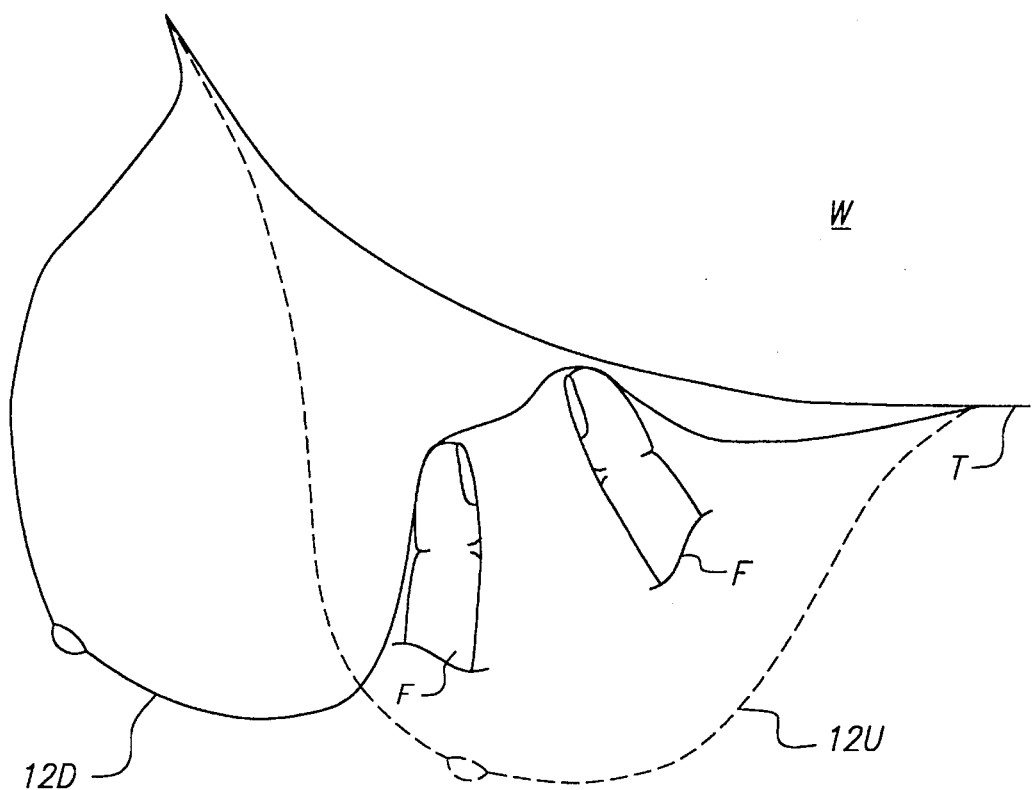
FIGS. 7, 8 and 9 exhibit cross-sectional diagrams of a female breast in floatation in overhead views. Both undetected and deflected conditions are shown in each drawing.
Figure 8:
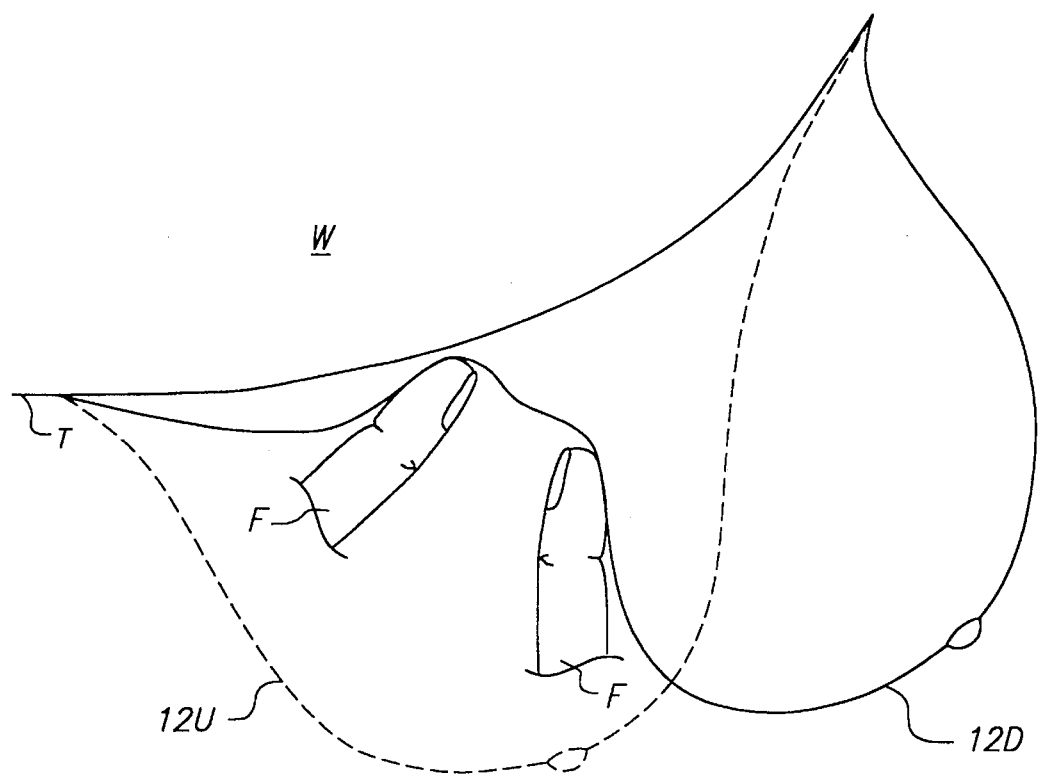
Figure 9:
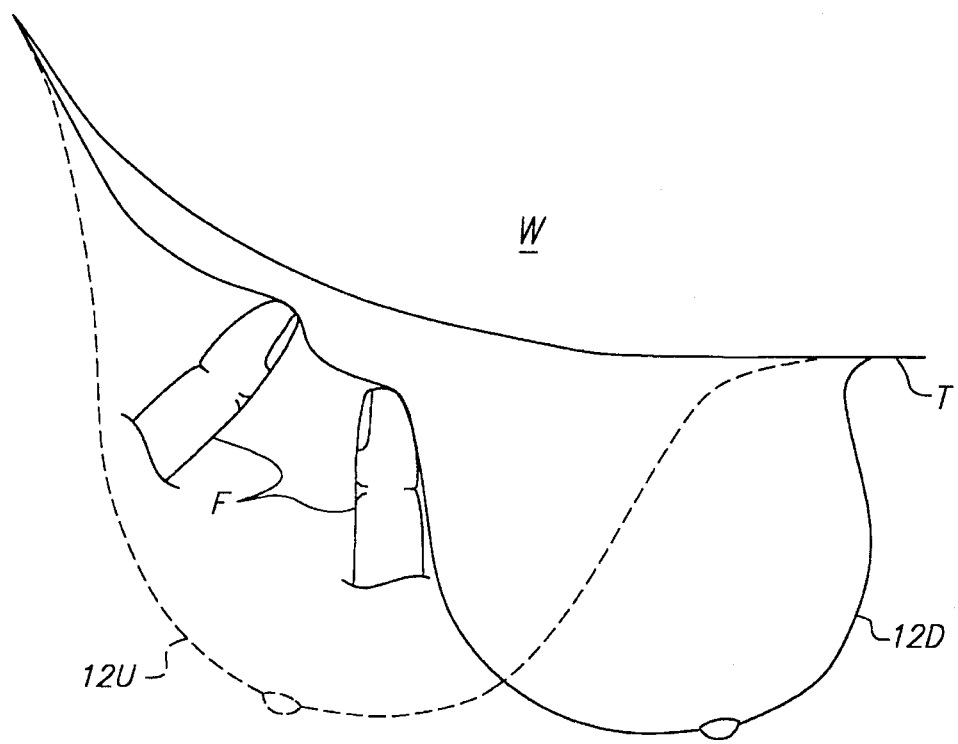

FIGS. 7, 8 and 9 furnish three additional overhead views of the patient during an examination. While the patient is sitting with her breasts immersed in an upright position and leaning forward slightly, the examiner uses his or her fingers F to gently probe the breast tissue. In FIG. 7, the examiner probes the patient's right breast (shaded) in the area of the rib cage. FIG. 8 illustrates an examination of the patient's left breast (shaded). FIG. 9 supplies yet another view of an examination of the patient's right breast (shaded).

Figure 10:
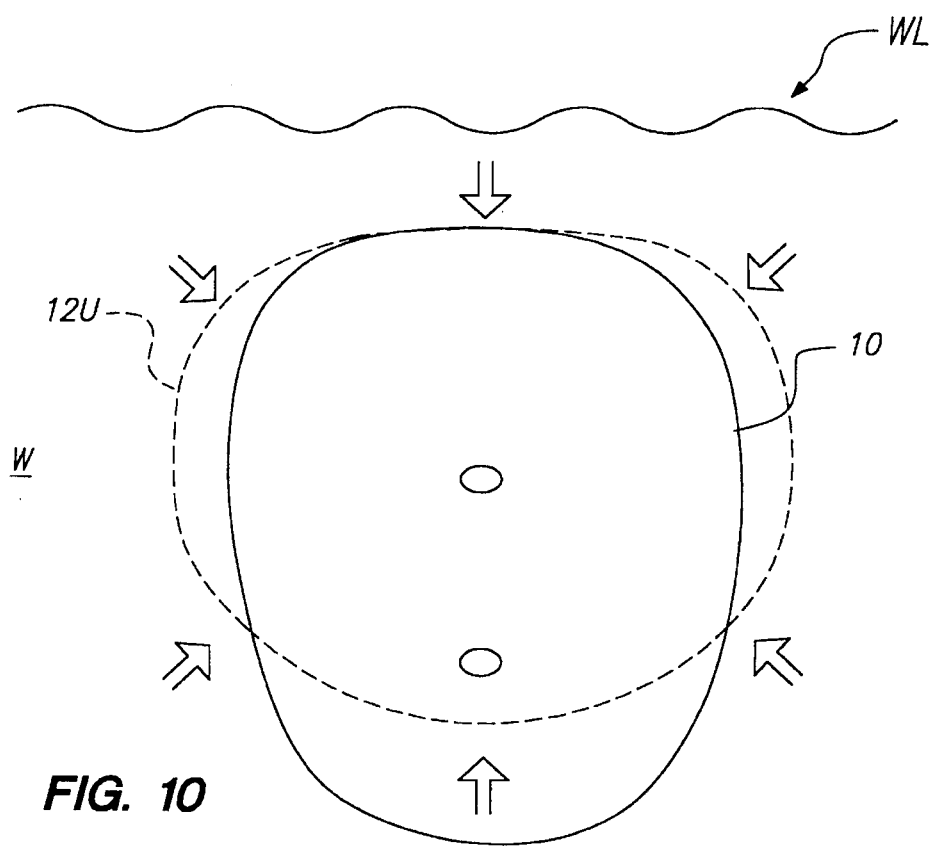
FIG. 10 supplies frontal view of a female breast both under the effects of floatation and under non-floatation conditions. This figure also exhibits the anticipated direction of the opposed fingers in the Finger Walk$^{SM}$ method of examination.

FIG. 10 supplies front view of a female breast, both under the effects of floatation and under non-floatation conditions. The arrows in FIG. 10 represent positions around the circumference of the breast where the examiner may place his or her fingers to begin the Finger Walk$^{SM}$ method. In one embodiment of the invention, the examiner places the fingers from each hand at opposite positions of the generalized "circle" formed by the periphery of the breast where it meets the torso. As a convenient reference, the unmarked arrows in FIG. 10 may be associated with the hour positions of the clock. "Opposite pairs of positions" means twelve and six o'clock, one and seven o'clock and four and ten o'clock et al. The examiner would first perform an examination starting at one of the opposite pairs, and then proceed around the circumference of the breast to perform a complete test for abnormalities as may be necessary.

The floatation influence of the water bath on the breast permits the examiner to gently move the breast tissue to one side so that tissue immediately adjacent to the breast may be tested for abnormalities. By moving the breast to one side, the examiner may also gain access to testing the tissues beneath the breast which are adjacent to the rib cage.

Figure 11:
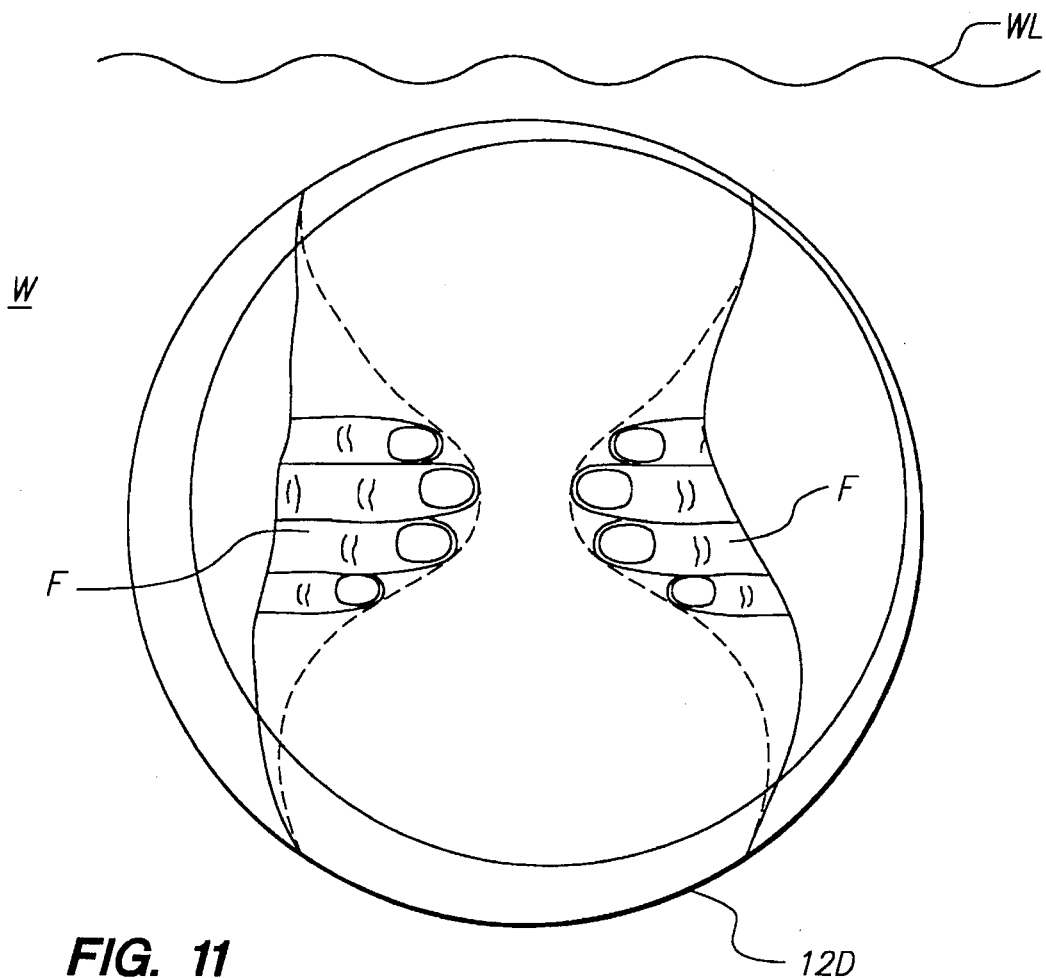
FIG. 11 depicts from views of the breast during an examination that shows the fingers from each hand in an opposed juxtaposition.
Figure 12:
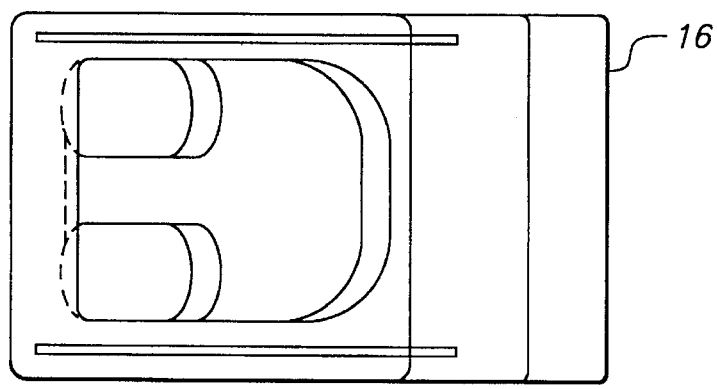
FIGS. 12, 13, 14, 15 and 16 offer top and cut-away side views of a floatation spa tub 16 which may be used to practice the Finger Walk$^{SM}$ examination method.
Figure 13:
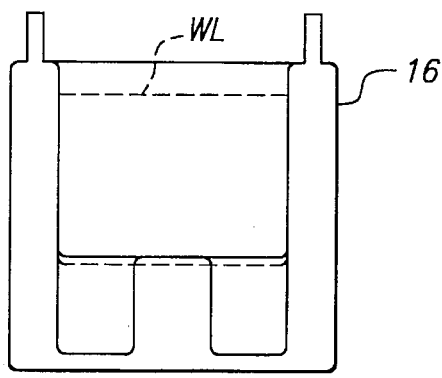
Figure 14:
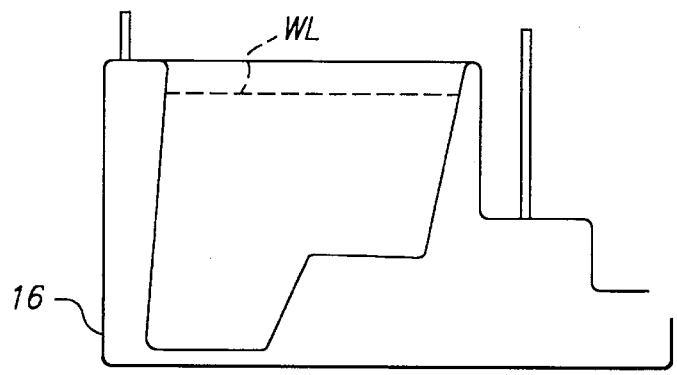
Figure 15:
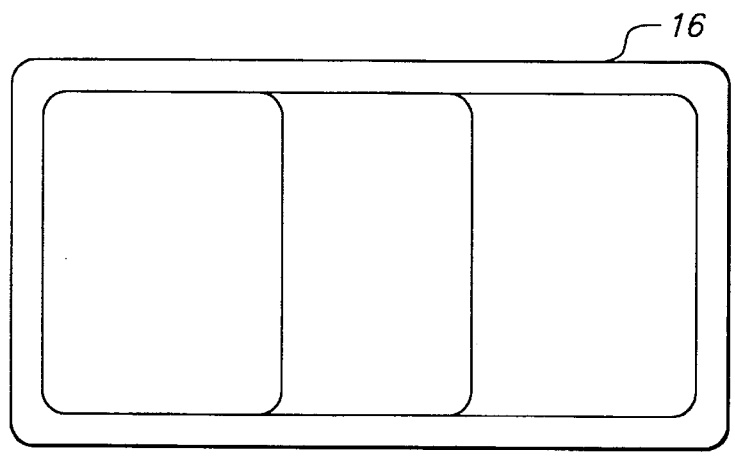
Figure 16:
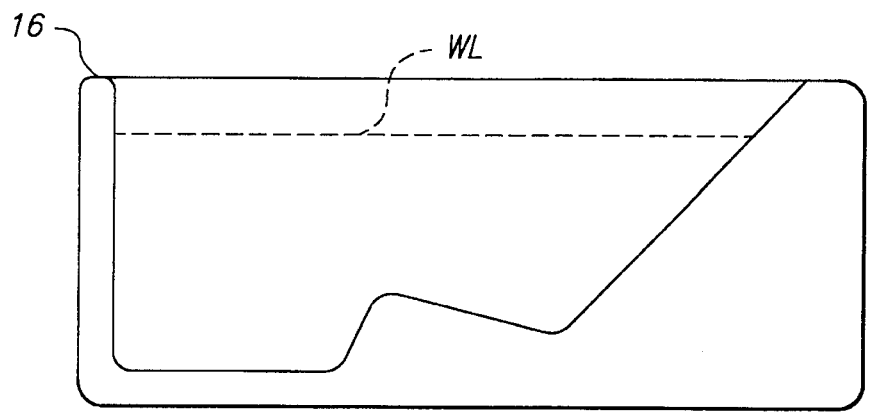

FIG. 11 depicts from views of the breast during an examination that utilizes several fingers from each hand. In general, the three index fingers are employed to perform an examination.

Figure 17:
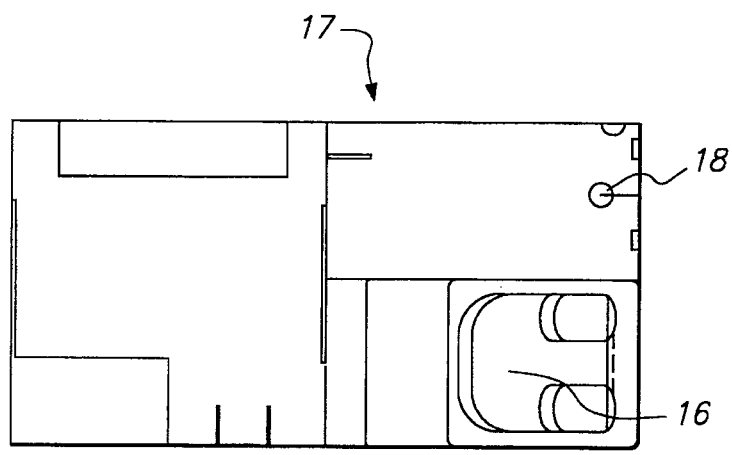
FIGS. 17, 18 and 19 furnish plan and elevational views of various embodiments of a modular spa facility 17 that includes both a tub 16 and a shower 18 which may be used to practice the present invention.
Figure 18:
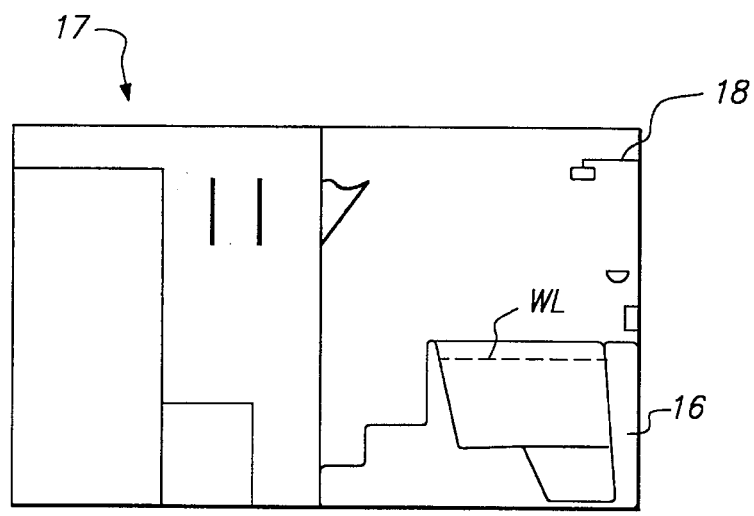
Figure 19:
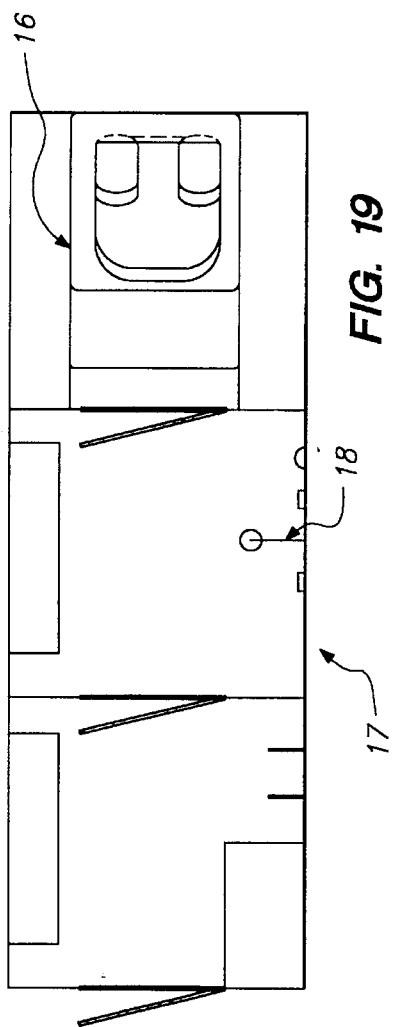

FIGS. 12, 13, 14, 15 and 16 offer top and cut-away side views of a floatation spa tub 16 which may be used to practice the Finger Walk$^{SM}$ examination method. FIGS. 17, 18 and 19 furnish plan and elevational views of various embodiments of a modular spa facility that includes a tub 16 and a shower 18 which may be used to practice the present invention.

Figure 20:
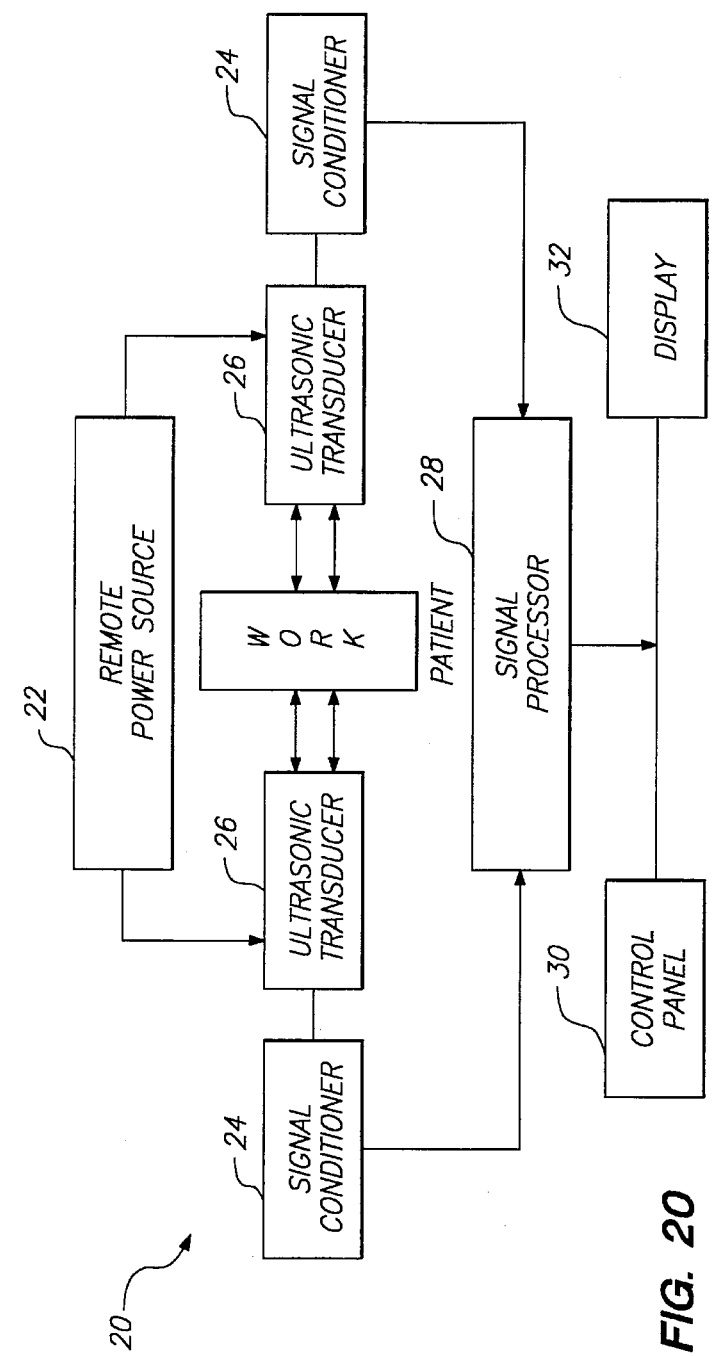
FIG. 20 is a schematic block diagram that depicts the ultrasonic apparatus that may be used to implement the invention.

FIG. 20 is a schematic block diagram that depicts apparatus that is well known to persons ordinarily skilled in the ultrasonic imaging art that may be used to implement the invention. Diagram 20 includes a remote power source 22 coupled to ultrasonic transducers 26. A signal is produced by the transducers 26 which is processed by signal conditioners 24 and signal processors 28 to form an image of the patient's body tissues. The image is generated on a display 32. The electronic equipment is operated by switches on a control panel 30.

Figure 21:
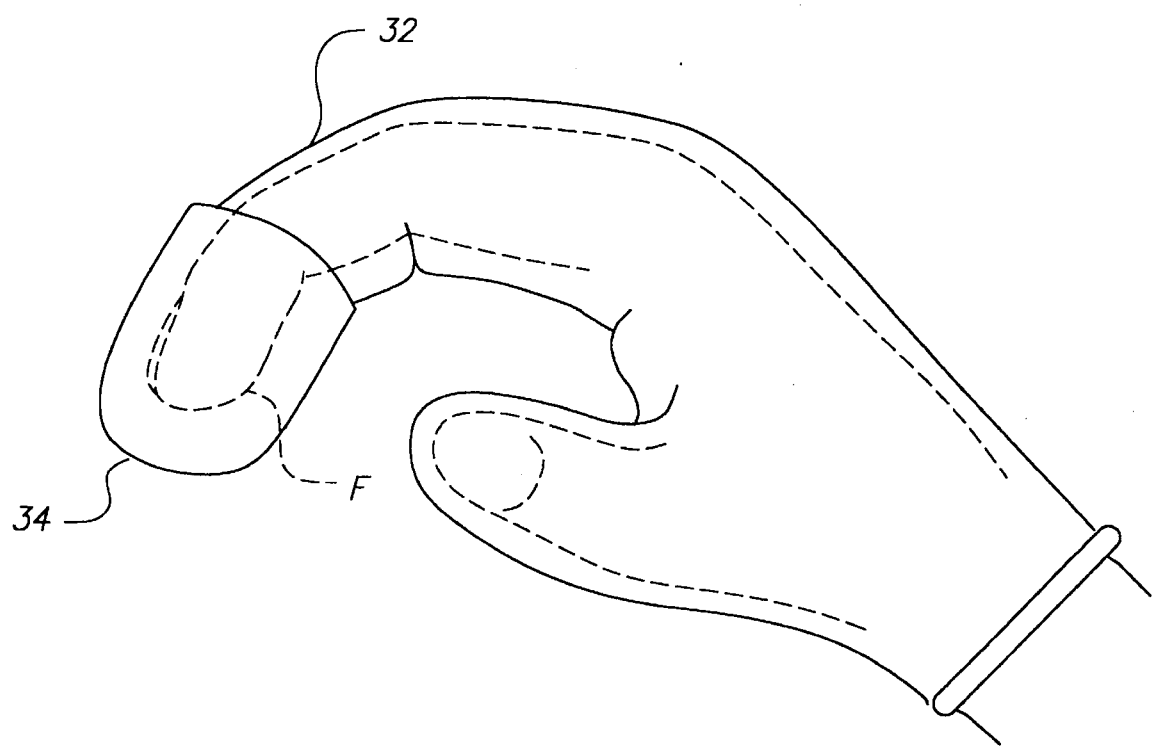
FIG. 21 is a schematic view of an ultrasonic transducer mounted in the finger of a glove that may be used to implement the invention.

FIG. 21 is a schematic view of an ultrasonic transducer mounted in the finger cup 34 of a glove 32 that may be used to implement the invention.

Figure 22:
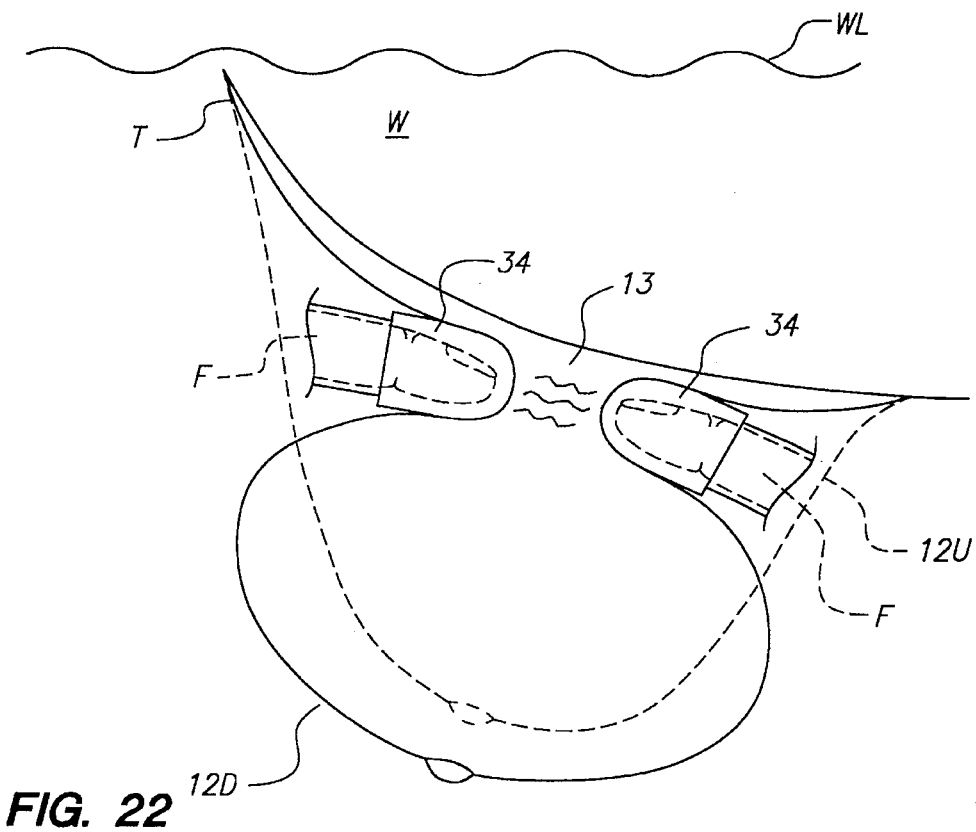
FIGS. 22 and 23 are superimposed views of a breast in both undeflected and deflected conditions. The view in each figure which represents the breast in floatation shows the tissue in a deflected condition during an examination that utilizes the transducer shown in FIG. 21.
Figure 23:
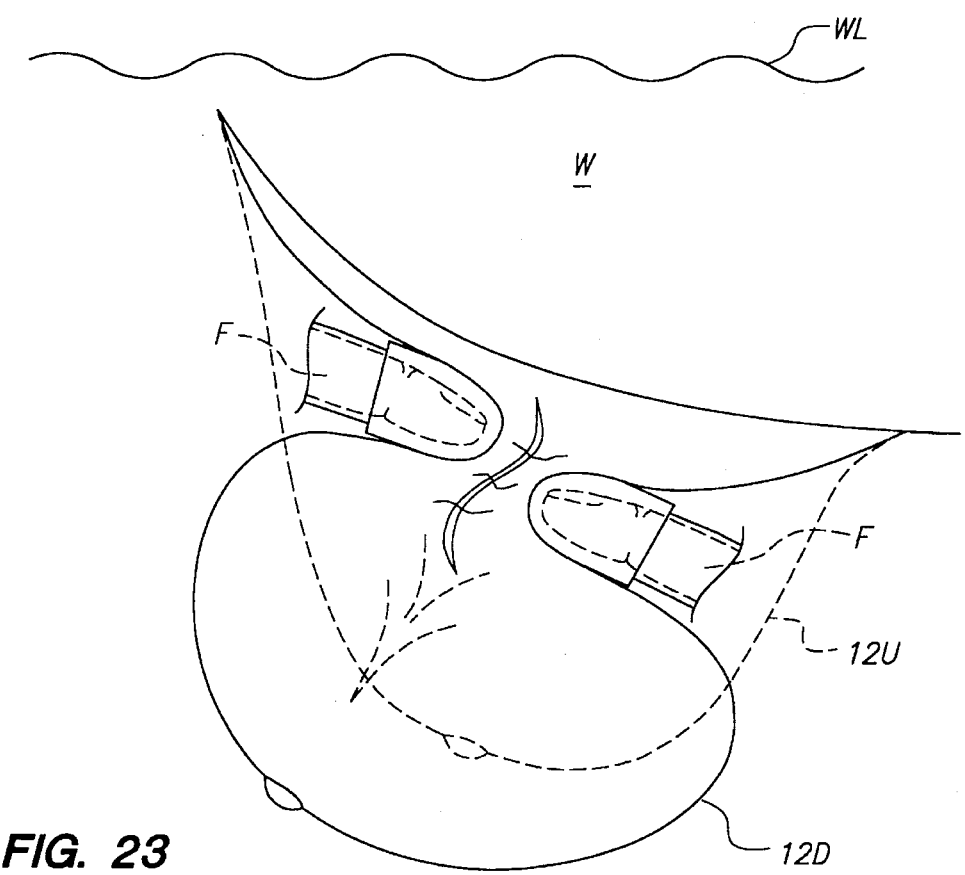

FIGS. 22 and 23 are superimposed views of a breast in both undetected 12U and deflected 12D conditions. The view in each figure which represents the breast in floatation shows the tissue in a deflected condition during an examination that utilizes the finger cup transducer 34 shown in FIG. 21.

Figure 24:
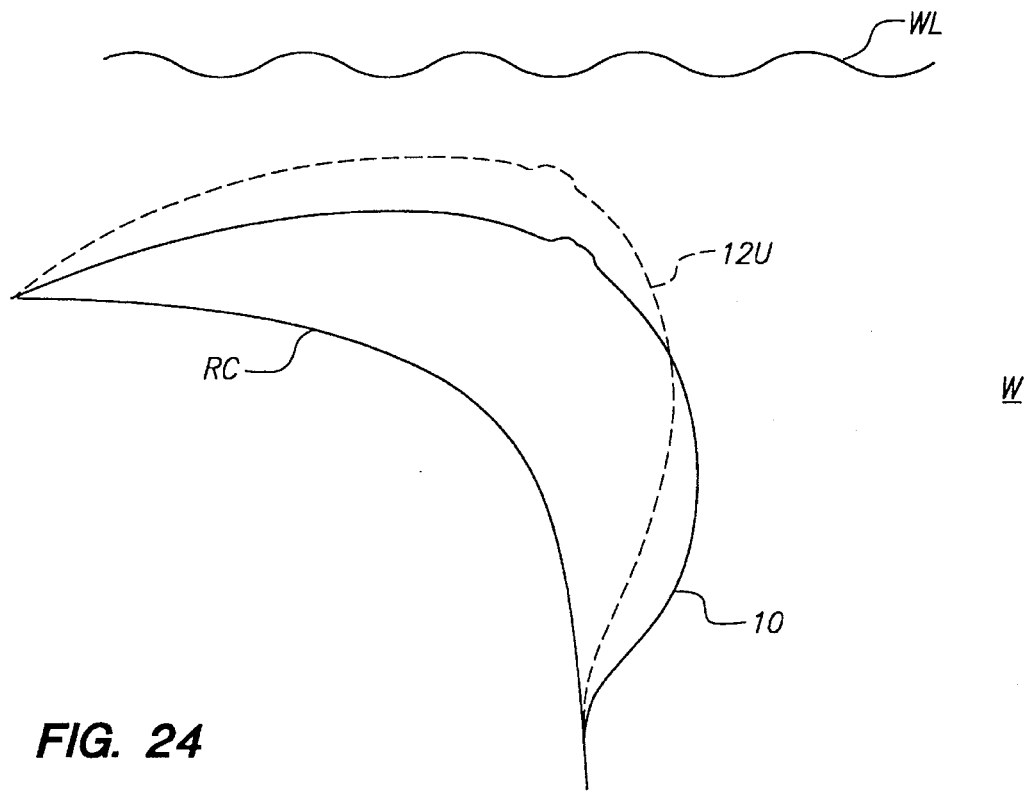
FIG. 24 provides views of a female breast while the patient is in a supine position.
Figure 25:
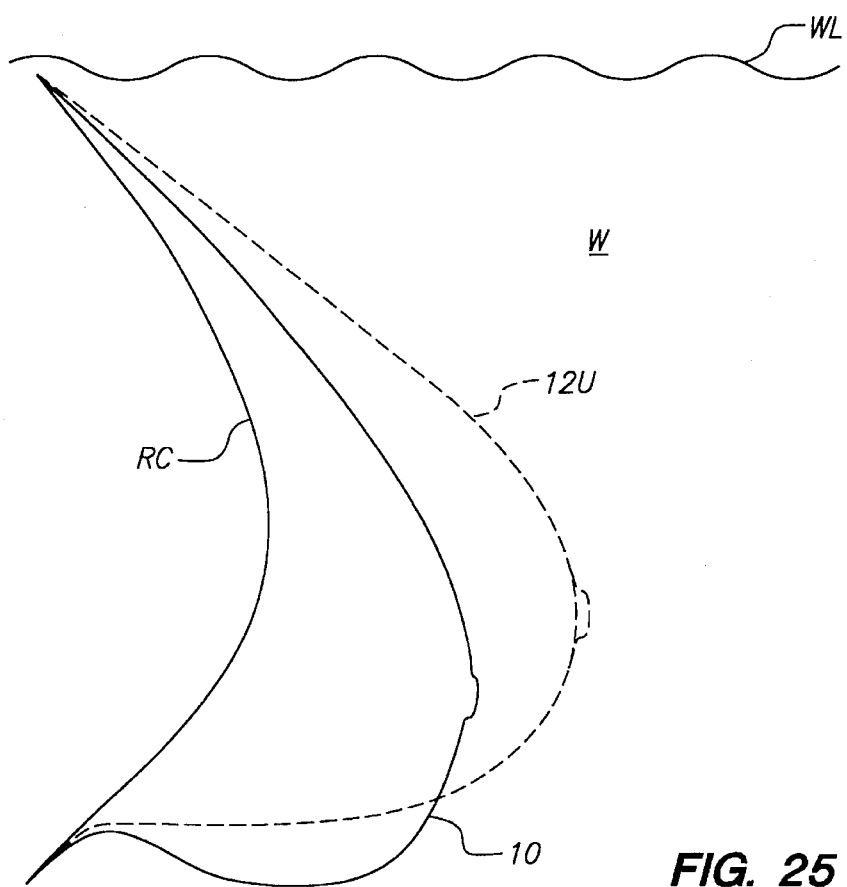
FIG. 25 provides views of a female breast with the patient in a supine position, but with the rib cage rotated outward approximately forty-five degrees.

FIG. 24 presents two different views of a female breast while the patient is in a supine position, with the patient flat on her back. As best seen in FIG. 24, without being immersed in water W, the breast would normally occupy the position indicated by reference character 10. When the breast is immersed below the water line WL, it is levitated and occupies the position indicated by reference character 12U. In either case, the contour of the rib cage is represented by reference character RC. FIG. 25 furnishes a pair of views of a female breast in both the normal 10 and levitated 12U positions when the patient is in a supine position, but with the rib cage rotated outward approximately forty-five degrees. This position is especially useful for examining the pectoral area under the arm pits after a breast is gently moved to one side with one hand while probing is accomplished with the other hand.

Figure 26:
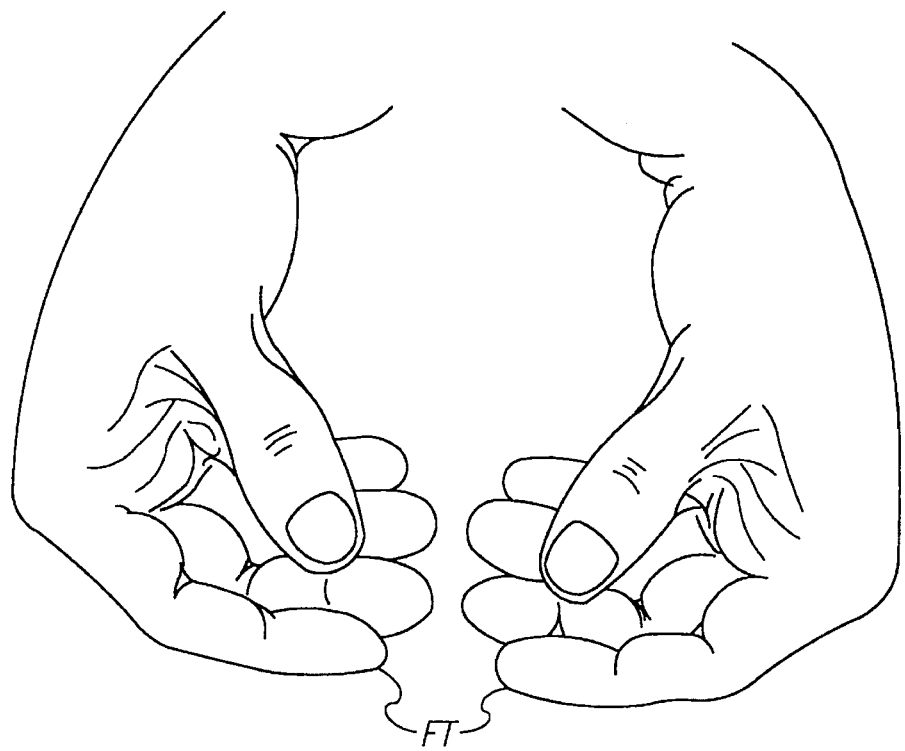
FIGS. 26, 27 and 28 illustrate the positions of the examiner's hands and fingers during the examination procedure embodied by the present invention.
Figure 27:
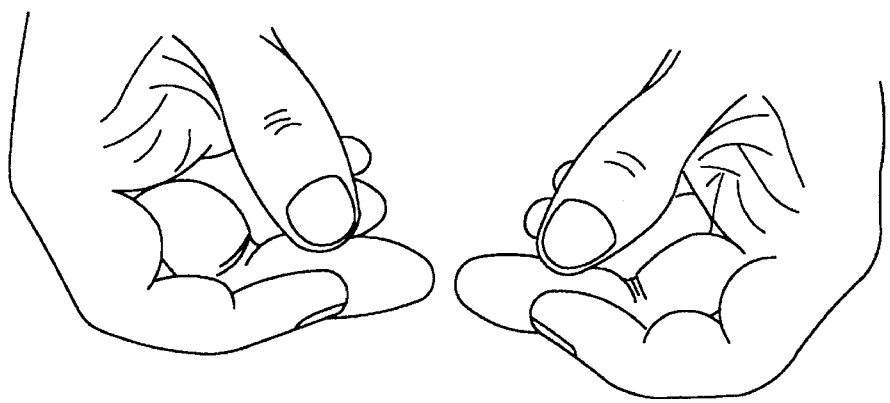
Figure 28:
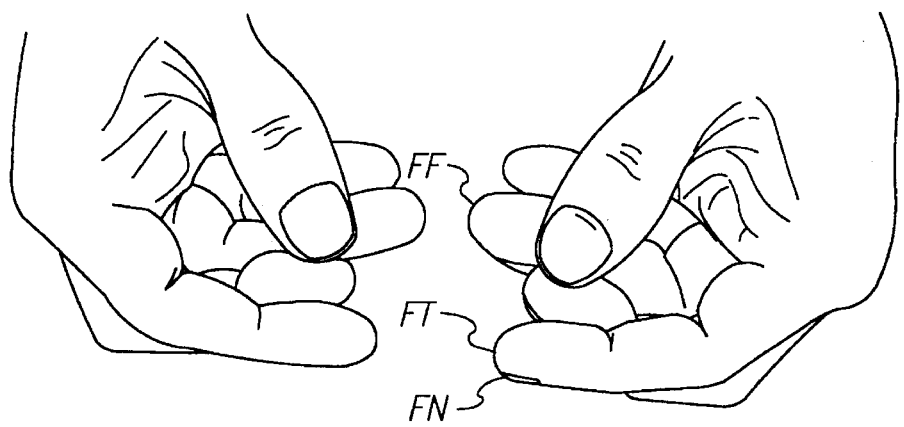

FIGS. 26, 27 and 28 reveal the placement and motion of the hands and the fingers according to a preferred embodiment of the present invention. In FIG. 26, the fingers F are generally in-line and occupy a normal extended position. In FIG. 27, the middle fingers F of both hands are extended toward each other. In FIG. 28, the middle fingers F move in and out slightly in a gentle repetitive motion, permitting the internal breast structure to readjust to penetration by the fingers. This readjustment enhances the ability of the examiner to detect abnormalities. FIG. 28 also identifies the area of the examiner's finger F that is used to perform the Finger Walk$^{SM}$ Method. The present invention relies on the enhanced sensitivity of the small portion of the finger tip FT that lies immediately below the fingernail FN. The flat portion FF of the finger, which is located near the whorl of the fingerprint, is less sensitive than the finger tip FT, and is therefore not used to perform the Finger Walk$^{SM}$. Unlike previous breast examination techniques that employ the rotating action of the flat portion of the fingers, the present invention utilizes a series of palpitating motions.

Figure 29:
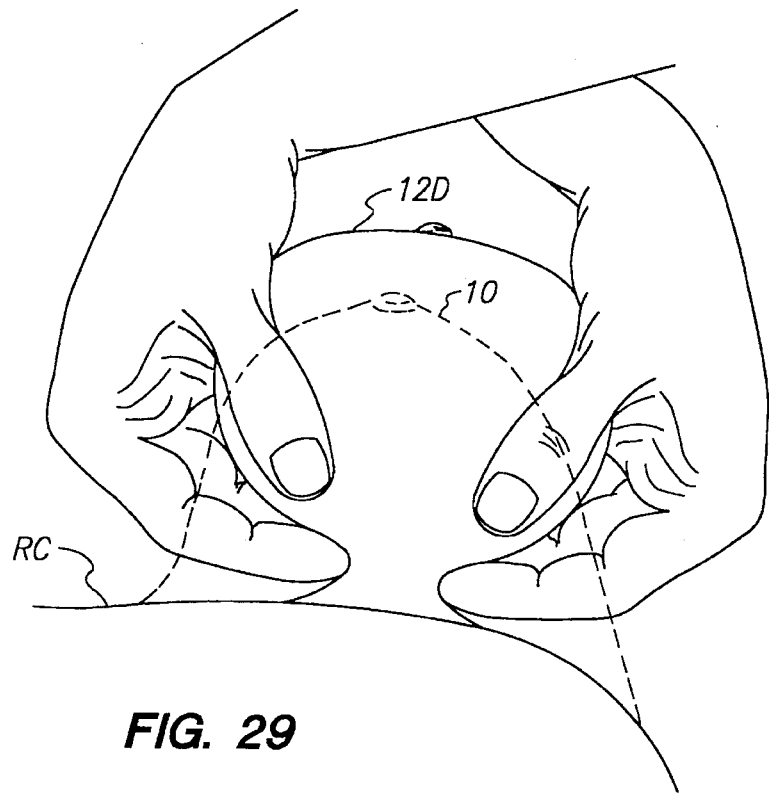
FIGS. 29, 30, 31, 32 and 33 comprise a series of sequential views of hand and finger positions that illustrate the Finger Walk$^{SM}$ method.
Figure 30:
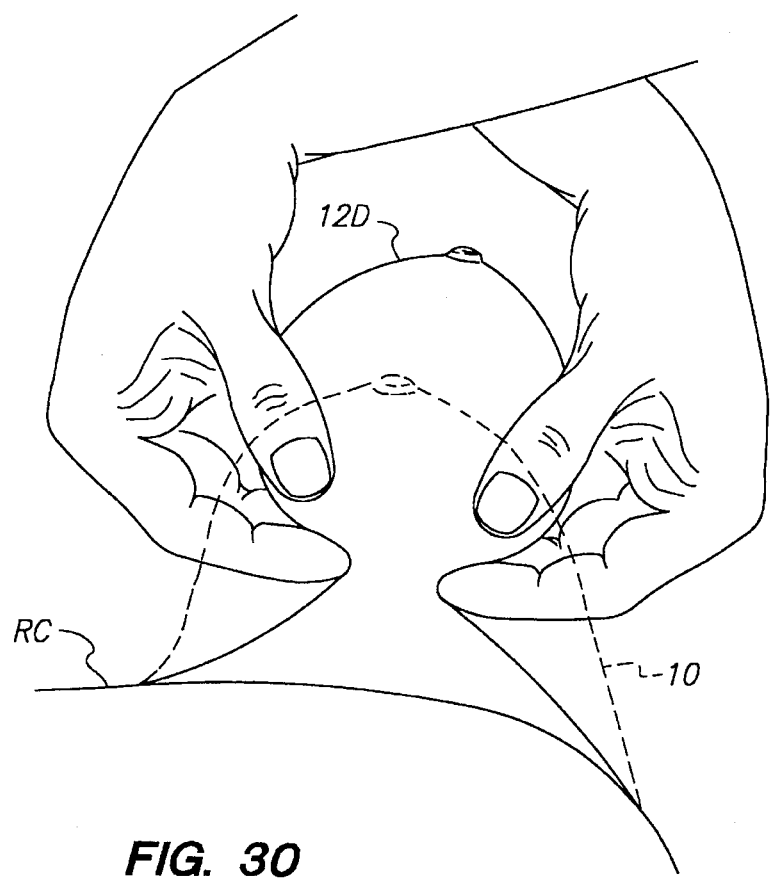
Figure 31:
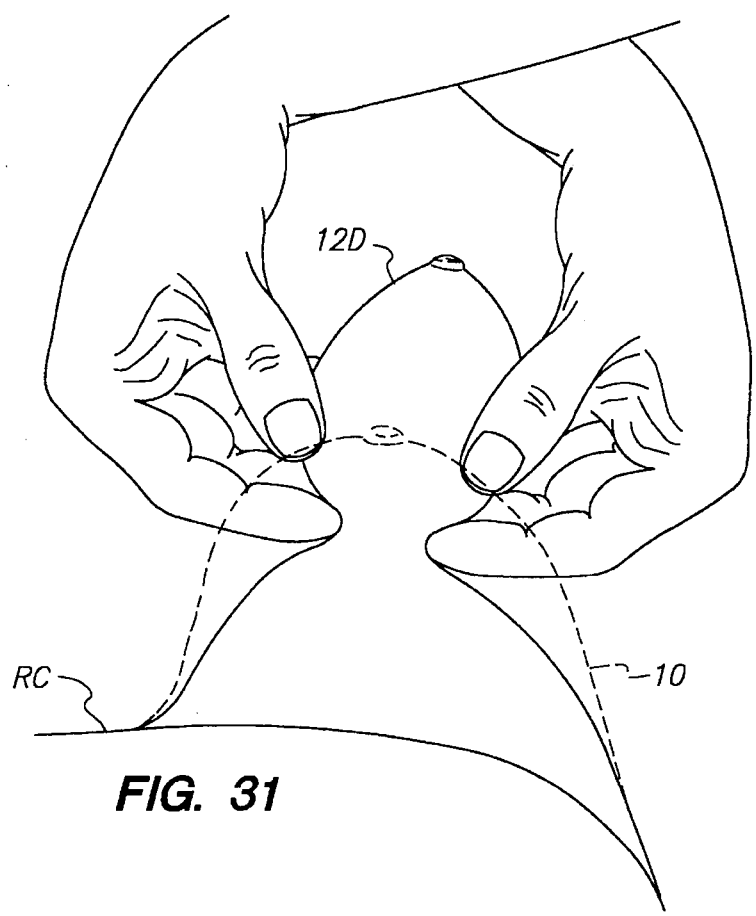
Figure 32:
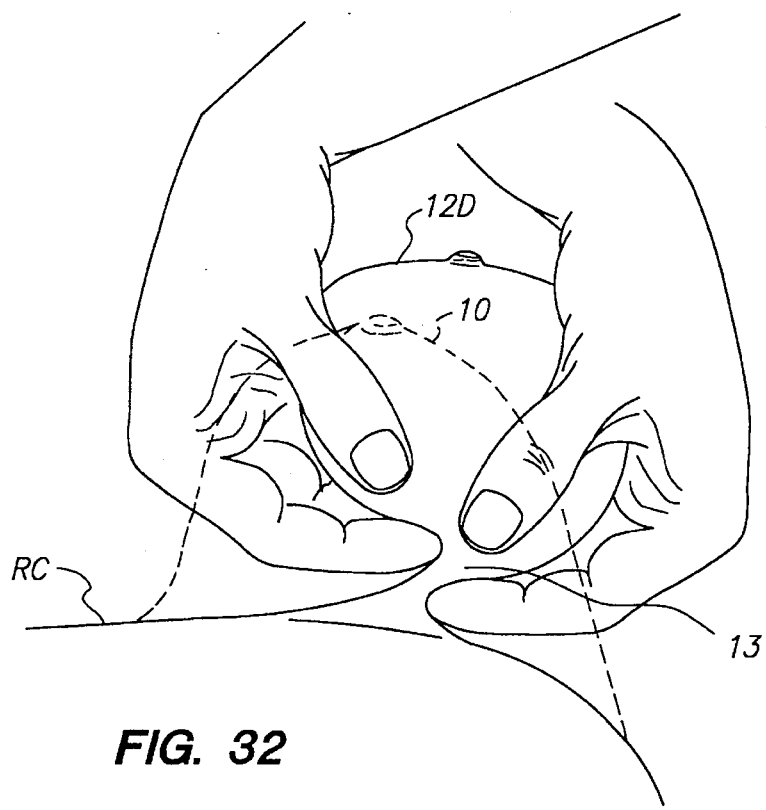
Figure 33:
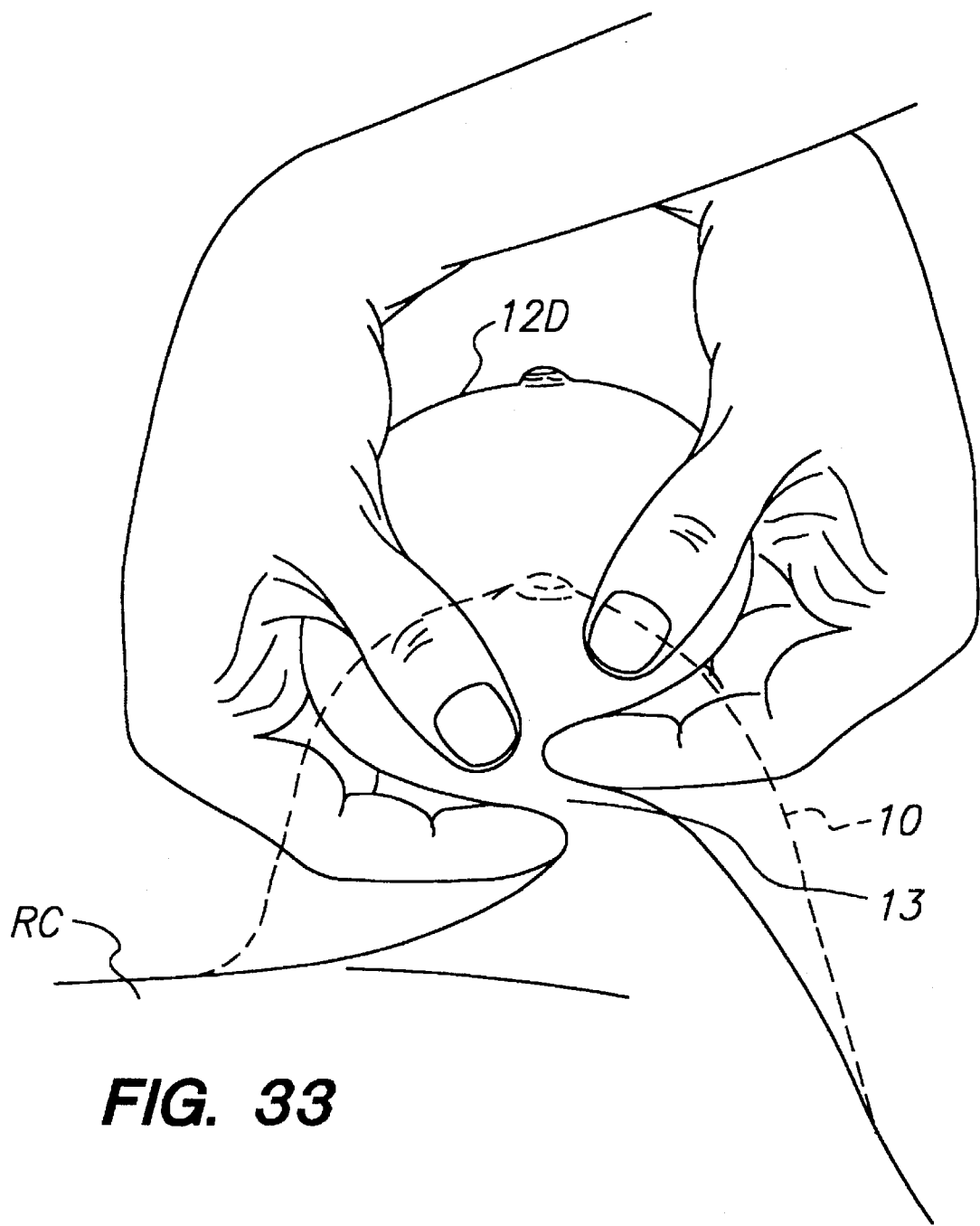

FIGS. 29 through 33 supply a sequence of illustrations of a Finger Walk$^{SM}$ procedure that is conducted while the patient is in an upright position, and leaning slightly forward. The perspective of FIGS. 29 through 33 is from a point above the patient's head, looking down into the water bath at her immersed breasts. FIG. 29 reveals a female breast on the right side of the torso in normal 10 and levitated and deflected positions 12D. A portion of the rib cage RC is shown along the base of the breast. FIG. 29 is an overhead view, depicting the crossed left and right hands of the examiner as he or she uses the fingers of both hands to constrict the lower portion of the breast. FIG. 30 shows the next stage of the Finger Walk$^{SM}$, depicting the breast in an extended position 12D. FIG. 31 offers a view of the breast in a hype-constricted position 12D. FIGS. 32 and 33 furnish two additional views of the examination process in which the examiner's fingers shape the patient's breast to form an constricted portion or "S-curve" 13 which enhances the sensitivity of the examiner to detect abnormalities. The examiner uses his or her hands so that the S-curve alternates from left to right and back and forth as may be required to perform a thorough examination.

Figure 34:
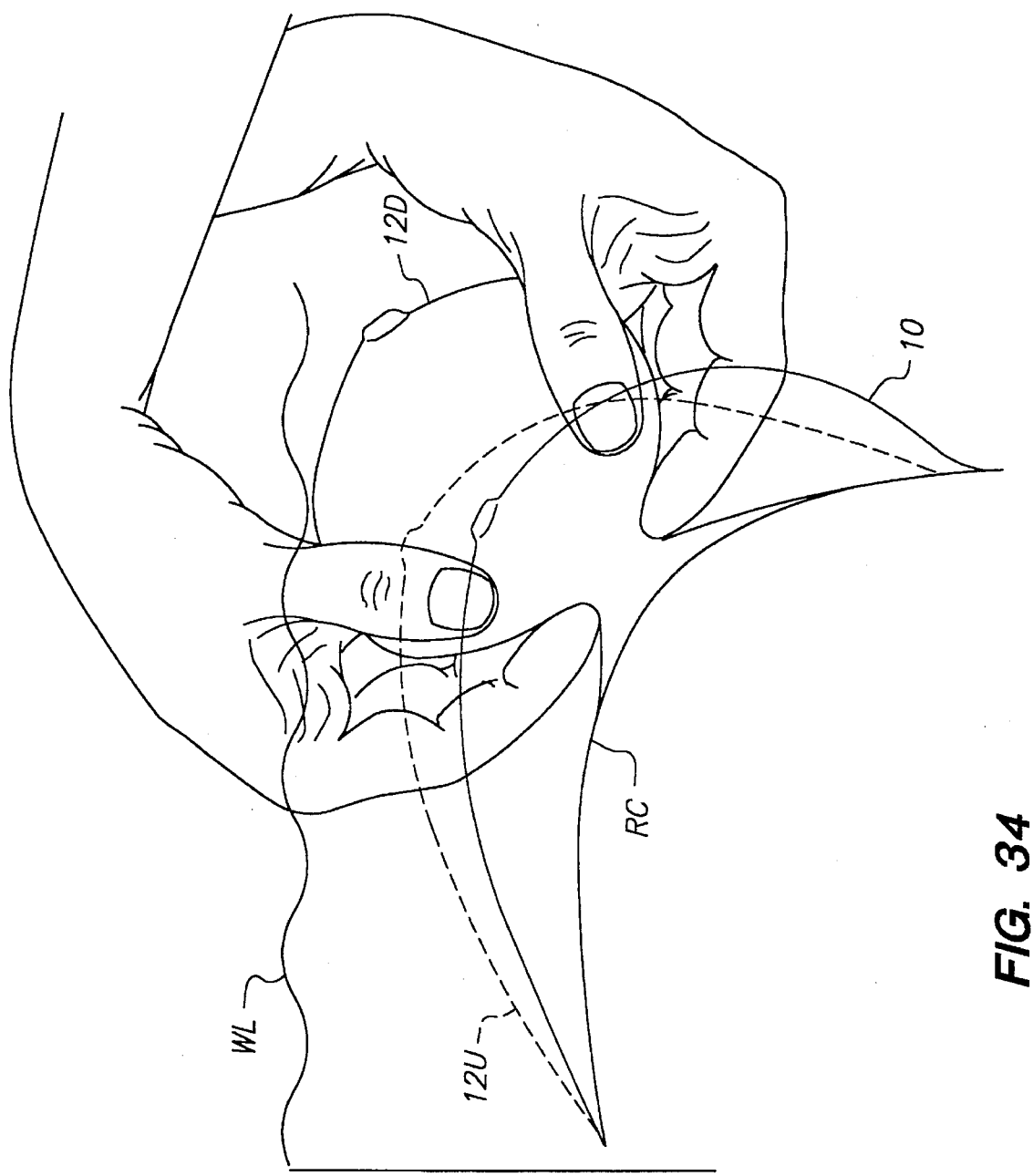
FIGS. 34 and 35 illustrate an examination procedure that is performed with the patient in a supine position with the rib cage rotated outward approximately forty-five degrees.
Figure 35:
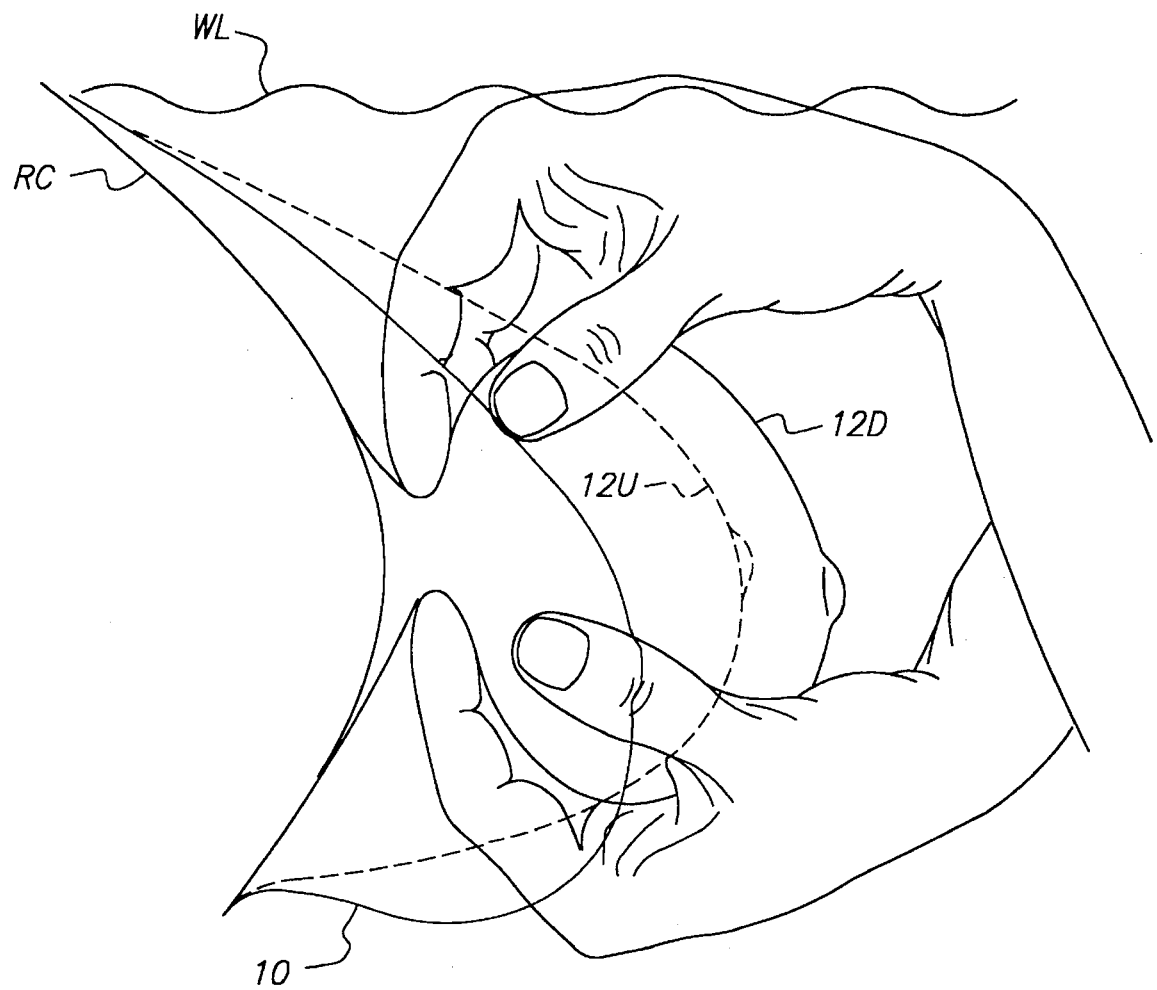

FIGS. 34 and 35 present side views of an examination performed while the patient's rib cage RC is rotated approximately forty-five degrees from a normal upright position.

Figure 36:
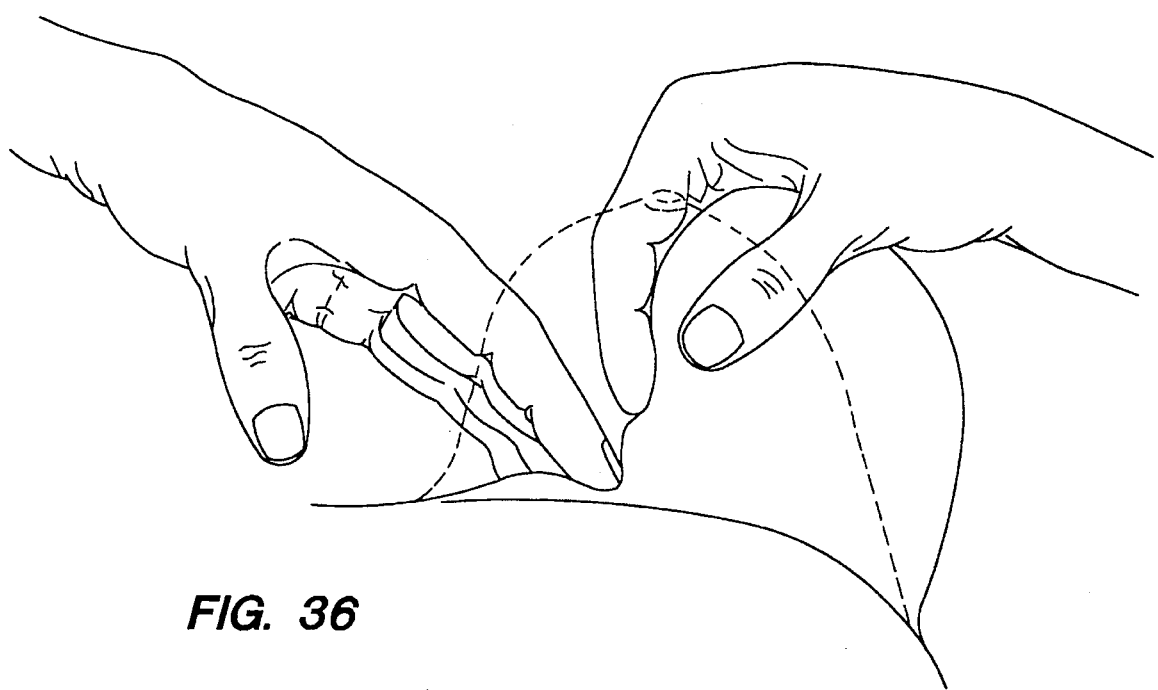
FIGS. 36 and 37 exhibit an examination procedure which is performed with the patient in an upright position.

FIG. 36 is an overhead view of an examination procedure in which the right breast is moved out to the patient's right to permit the examiner to probe the breast tissue near the rib cage with the finger tips of the left hand.

Figure 37:
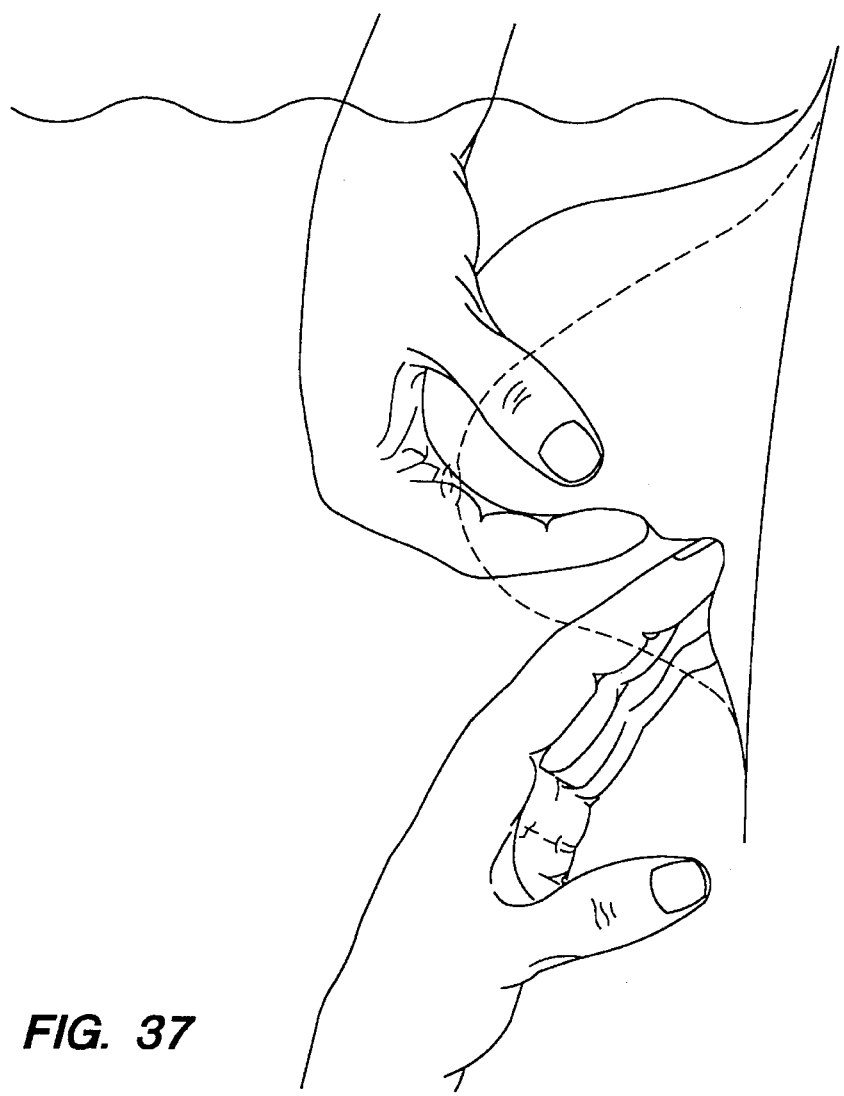

FIG. 37 is a side view which depicts an exam method in which the breast is lifted upward to access the tissue of the lower portion of the breast near the rib cage RC.

Making a Mold under Floatation for the Manufacture of Articles of Clothing

Figure 38:
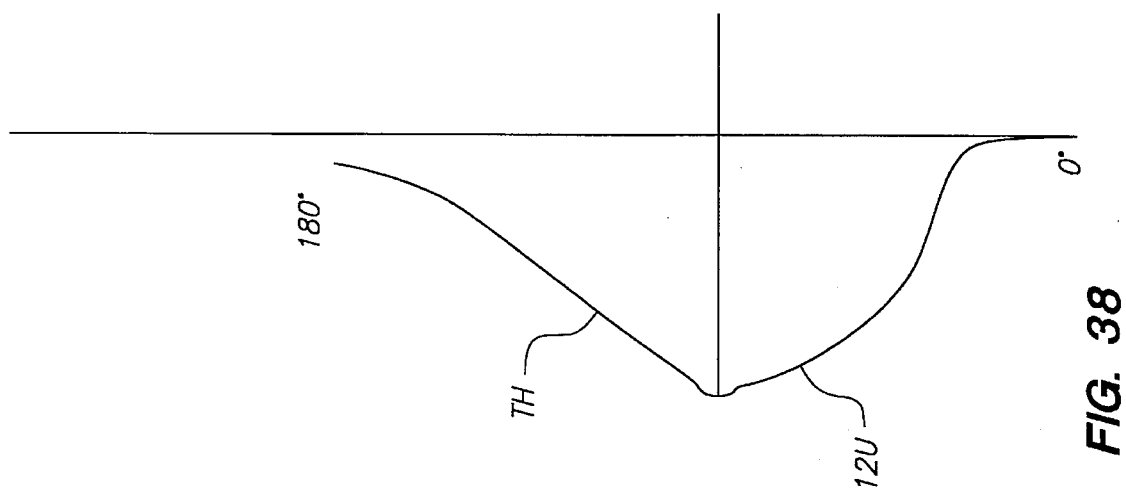

FIG. 38 is a cross-sectional plot of a female breast under floatation while the patient is in a prone position. FIG. 39 is a table that contains bust mold measurements that were obtained by making a three-dimensional mold of the breast shown in FIG. 38. Digitizing measurement equipment was then employed measure the surface of the mold to generate a numerical value for coordinate pairs of elevation and radial position. The lower portion of the cross-sectional plot is located at the zero degree (0) direction, while the upper portion is located at the one hundred and eighty degree (180) direction.

This method of making a mold of the breast under floatation is not only useful for making clothing which fits the natural contours of the breast, but is also a valuable tool for detecting abnormalities. Thickened portions TH of the breast tissue that are normally not readily detectable using conventional examination methods can be sensed using the method of the present invention.

Figure 40:
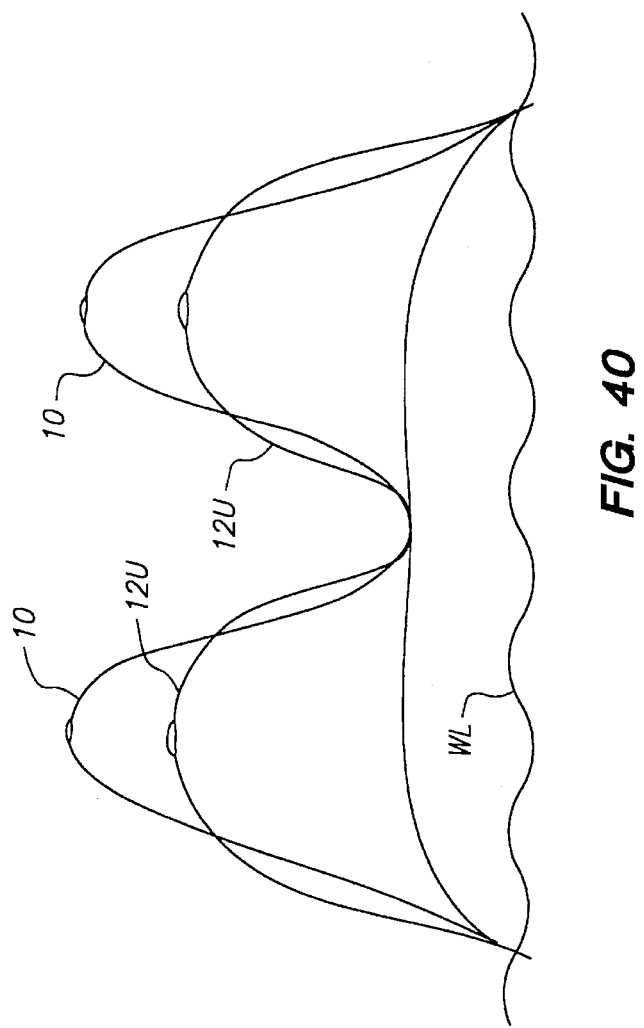
FIG. 40 is an overhead view of a patient in a prone position.

FIG. 40 is a diagram showing a patient partially immersed in water in a prone position from the perspective of an overhead position. The breasts are shown in both the distorted pendular shapes 10 which occur without the effects of floatation, and in their natural "perfect" shapes 12U which occur in the floatation environment.

Figure 41:
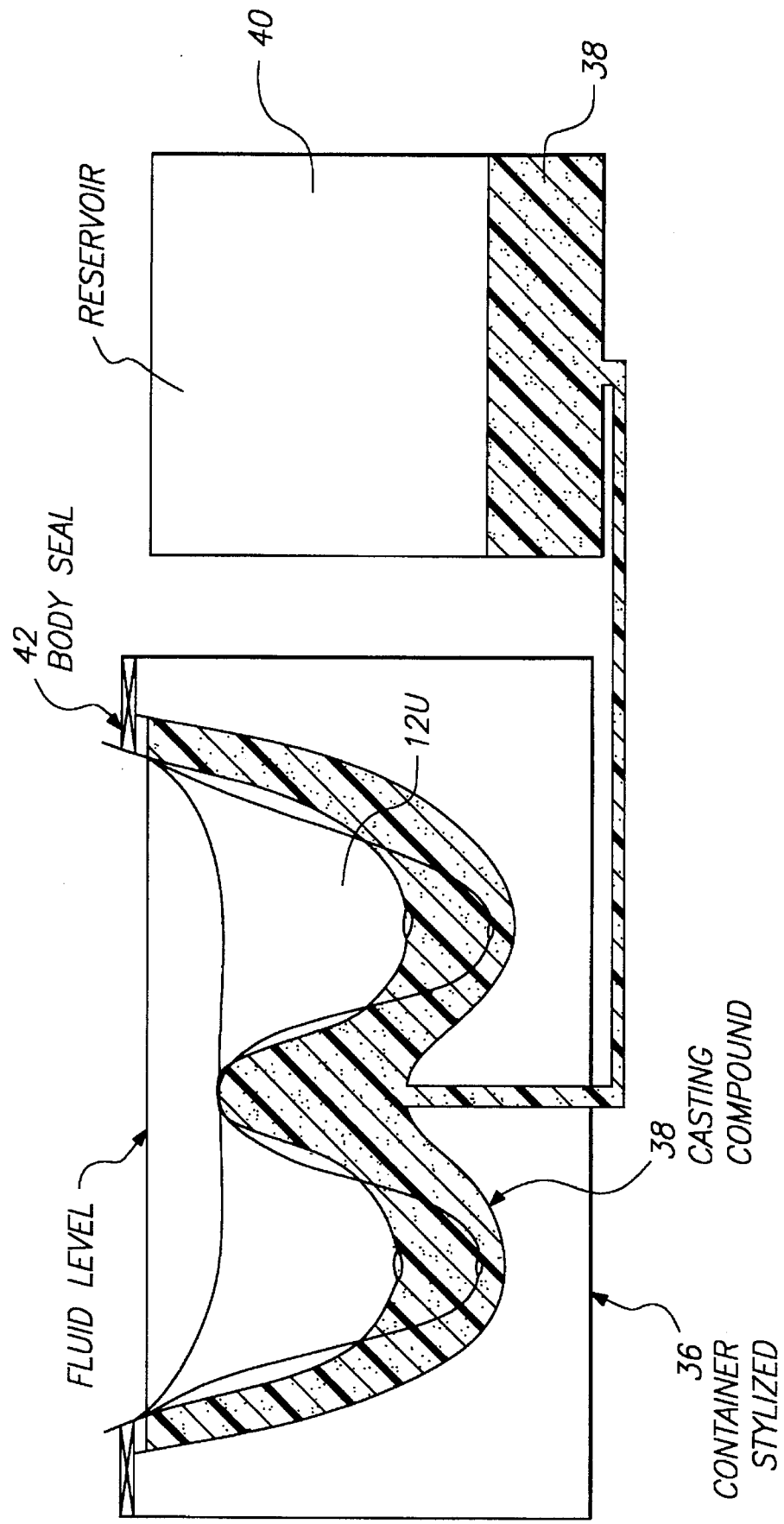
FIG. 41 is a front view of a container that is used to cast a mold of female breasts. The mold may be used to manufacture a bra, blouse, shirt or dress.

FIG. 41 is a front view of a container 36 that is used to cast a mold of female breasts. The container 36 is used to make a bust of the female breasts 12U. During the casting process, the patient is situated in the prone position. A liquid casting compound 38 flows into the container 36 from a reservoir 40. When the casting compound 38 enters the container 36, the breasts are placed under floatation. This causes the breasts to assume a nearly natural shape, since gravity has very little effect. The compound 38 is kept inside the container 36 by body seal 42. FIG. 42 is a side view of the container 36. In a preferred embodiment of the invention, a commercially available casting compound called Earthium Advanced Life Cast™ is utilized to manufacture the mold.

FIGS. 43 and 44 are side views of molds 44 and 46 produced by the casting process illustrated in FIGS. 41 and 42. The mold 44 shown in FIG. 43 is a "low-density" casting, because the particular mix of casting compound that was used to make this mold 44 had a specific gravity that was less than that of water. The mold 46 shown in FIG. 44 is a "high-density" casting, because the particular mix of casting compound that was used to make this second mold 46 had a specific gravity that was greater than that of water. Different mixtures of casting compounds may be composed to obtain castings of varying densities which, in turn, control the shape of the finished mold. The density and curing time of the completed mold is also affected by the ratios of the casting compound, the water, the water temperature and the catalyst. When the casting has a relatively low density, the breast extends relatively far away from the rib cage, and takes on a somewhat elongated shape. This increases the moment arm to the center of gravity of the breast, and increases the tension on the breast tissue caused by the forces of gravity. Conversely, when the casting has a relatively high density, the breast does not extend as far away from the rib cage, and takes on a more compact shape. The moment arm to the center of gravity of the breast is reduced, and the tension on the breast tissue caused by the forces of gravity are lowered.

Castings having different densities that produce different shapes are useful in detecting abnormalities in the breast tissue. When levitated in the prone position, the internal structure of the breast will seek its most natural position. Any abnormality in the breast tissue will create a distortion or have a protruding effect on the outer surface of the mold.

Castings of different shapes are also useful for producing various articles of clothing which can be custom fit to a particular breast shape. For example, the present invention may be utilized to manufacture a bra which reduces the strain on the breast tissue by reducing the moment arm to the center of gravity of the breast. A bra or breast inserts can be custom-designed to fit individual tastes or needs. The moment arm has a major role in the up and down motion of the breast in walking and running. Providing a custom fit bra contributes to good health and positive self-esteem.

CONCLUSION

Although the present invention has been described in detail with reference to particular preferred and alternative embodiments, persons possessing ordinary skill in the art to which this invention pertains will appreciate that various modifications and enhancements may be made without departing from the spirit and scope of the claims that follow. The imaging equipment that has been disclosed above is presented to educate the reader about particular embodiments, and is not intended to constrain the limits of the invention or the scope of the claims. The List of Reference Characters which follows is intended to provide the reader with a convenient means of identifying elements of the invention in the 10 specification and drawings. This list is not intended to delineate or narrow the scope of the claims.

LIST OF REFERENCE CHARACTERS

Female breast in normal pendent position
U Female breast immersed in water under influence of floatation in undetected position
12D Deflected position of breast during examination
Constricted portion of breast
Internal structure of breast
Spa tub
Modular spa facility
Shower
Schematic block diagram of ultrasonic breast evaluation equipment and circuitry
Remote power source
Signal conditioner
Ultrasonic transducer
Signal processor
Control panel
Glove containing transducer
Finger cup
Container
Reservoir
Casting compound
Body seal
Low density mold
High density mold
F Finger
FF Flat portion of finger
FN Finger nail
FT Finger tip
RC Rib cage
T Torso
W Water
WL Water level

What is claimed is:

1. A method of examining a portion of the human body of a person comprising the steps of:

immersing said portion of the human body in a bath of hot water which relaxes the tissues of said portion of the human body while said person is in a generally upright position;

examining said portion of the human body under the levitating influence caused by the immersion of said portion of the human body in said bath of hot water;

applying a random, repetitive, palpating and probing pressure using the tips of the fingers (FT) from both of the examiner's hands; and applying pressure using the finger tips (FT) to form an "S-curve" deflection of said portion of the human body which is placed between said finger tips (FT) which occupy generally opposed positions.

2. A method as claimed in claim 1, in which said step of examining said portion of the human body is performed with the finger tips of both hands simultaneously while the finger tips are in generally opposing positions.

3. A method as claimed in claim 1, in which said hot water (W) has a temperature in the approximate range of from 101 to 104 degrees Fahrenheit.

4. A method as claimed in claim 1, in which palpation by said finger tip (FT) from each hand begins at diametrically opposed positions around the circumference of said portion of the human body, and proceeds sequentially around the circumference of said portion of the human body until the examination is complete.

5. A method as claimed in claim 1, in which the levitating influence caused by the immersion of said portion of the human body in said fluid enables a self-examination of tissue immediately adjacent to and underneath said portion of the human body.

6. A method as claimed in claim 1, in which said person is in a generally upright position and is leaning forward slightly.

7. A method as claimed in claim 1, in which the person is leaning forward at an angle of approximately five to fifteen degrees.

8. A method as claimed in claim 1, in which the person's rib cage is rotated approximately forty-five degrees from said generally upright position.

9. A method as claimed in claim 1, in which said portion of the human body is a breast.

10. A method as claimed in claim 1, in which said portion of the human body is an abdomen.

11. A method as claimed in claim 1, in which said portion of the human body includes a male testicle.

12. A method as claimed in claim 1, in which a male abdomen is probed to detect a hernia.

* * * * *

UNITED STATES PATENT AND TRADEMARK OFFICE
CERTIFICATE OF CORRECTION

PATENT NO. : 5,572,995        Page 1 of 4

DATED : November 12, 1996

INVENTOR(S) : Roderick G. Rohrberg

It is certified that error appears in the above-identified patent and that said Letters Patent is hereby corrected as shown below:

Column 2, line 37:    "an" should be --a--.

Column 3, line 41:    "embodiment" should be --embodiments--.

Column 3, line 66:    between "supplies frontal" insert --a--.

Column 4, line 4:    "from" should be --front--.

Column 4, line 54:    between "castings a" insert --of--.

Column 6, line 11:    "represented" should be --represents--.

Column 6, line 14:    after "way", insert --,--.

Column 6, line 25:    after "supplies" insert --a--.

Column 6, line 47:    "from" should be --front--.

Column 8, line 8:    "exam" should be --examination--.

Column 8, line 18:    between "employed measure" insert --to--.

Column 8, line 20:    "position" should be --positions--.

UNITED STATES PATENT AND TRADEMARK OFFICE
CERTIFICATE OF CORRECTION

PATENT NO.   :   5,572,995

DATED   :   November 12, 1996

INVENTOR(S)   :   Roderick G. Rohrberg

It is certified that error appears in the above-identified patent and that said Letters Patent is hereby corrected as shown below:

Column 9, line 39:   please delete "10".

Column 9, line 43:   before "Female" insert --10--.

Column 9, line 44:   before "U" insert --12--.

Column 9, line 47:   before "Constricted" insert --13--.

Column 9, line 48:   before "Internal" insert --14--.

Column 9, line 49:   before "Spa" insert --16--.

Column 9, line 50:   before "Modular" insert --17--.

Column 9, line 51:   before "Shower" insert --18--.

Column 9, line 52:   before "Schematic" insert --20--.

Column 9, line 54:   before "Remote" insert --22--.

Column 9, line 55:   before "Signal" insert --24--.

Column 9, line 56:   before "Ultrasonic" insert --26--.

UNITED STATES PATENT AND TRADEMARK OFFICE
CERTIFICATE OF CORRECTION

PATENT NO. : 5,572,995

DATED : November 12, 1996

INVENTOR(S) : Roderick G. Rohrberg

It is certified that error appears in the above-indentified patent and that said Letters Patent is hereby corrected as shown below:

Column 9, line 57: before "Signal" insert --28 --.

Column 9, line 58: before "Control" insert --30 --.

Column 9, line 59: before "Glove" insert --59 --.

Column 9, line 60: before "Finger" insert --34 --.

Column 9, line 61: before "Container" insert --36 --.

UNITED STATES PATENT AND TRADEMARK OFFICE
CERTIFICATE OF CORRECTION

PATENT NO. : 5,572,995

DATED : November 12, 1996

INVENTOR(S) : Roderick G. Rohrberg

It is certified that error appears in the above-indentified patent and that said Letters Patent is hereby corrected as shown below:

Column 9, line 62:  before "Reservoir" insert --38 --.

Column 9, line 63:  before "Casting" insert --40 --.

Column 9, line 64:  before "Body" insert --42 --.

Column 9, line 65:  before "Low" insert --44 --.

Column 10, line 1:  before "High" insert --46 --.

Signed and Sealed this

Tenth Day of June, 1997

Attest:

BRUCE LEHMAN

Attesting Officer

Commissioner of Patents and Trademarks